(12) United States Patent
Alanine et al.

(10) Patent No.: US 6,184,236 B1
(45) Date of Patent: Feb. 6, 2001

(54) METHOD OF TREATING A NEURODEGENERATIVE DISEASE BY ADMINISTERING AN ARYL-CYCLOHEXYLAMINE DERIVATIVE

(75) Inventors: Alexander Alanine, Riedisheim (FR); Bernd Büttelmann, Schopfheim (DE); Marie-Paule Heitz Neidhart, Hagenthal le Bas; Emmanuel Pinard, Linsdorf, both of (FR); René Wyler, Zürich (CH)

(73) Assignee: Hoffmann-La Roche Inc., Nutley, NJ (US)

( * ) Notice: Under 35 U.S.C. 154(b), the term of this patent shall be extended for 0 days.

(21) Appl. No.: 09/370,602

(22) Filed: Aug. 9, 1999

(30) Foreign Application Priority Data

Aug. 18, 1998 (EP) .................................................. 98115484

(51) Int. Cl.[7] ...................... A61K 31/445; A61K 31/335; A61K 31/18; A61K 31/135
(52) U.S. Cl. .......................... 514/329; 514/452; 514/603; 514/605; 514/647
(58) Field of Search .................................. 514/329, 452, 514/603, 605, 647

(56) References Cited

U.S. PATENT DOCUMENTS

| 5,260,318 | 11/1993 | Lubisch et al. . |
| 5,296,485 | 3/1994 | Lubisch et al. . |

FOREIGN PATENT DOCUMENTS

| 0 481 299 B1 | 4/1992 | (EP) . |
| 0 503 411 B1 | 9/1992 | (EP) . |
| WO97/15549 | 5/1997 | (WO) . |

OTHER PUBLICATIONS

Abstract, Acc No. 97–271749/199724 (Abstract of WO97/15549), 1997.

Primary Examiner—William R. A. Jarvis

(74) Attorney, Agent, or Firm—George W. Johnston; Patricia S. Rocha-Tramaloni; Eileen M. Ebel

(57) ABSTRACT

The present invention provides a method of treatment of a disease associated with neurodegeneration by administering a therapeutically effective amount of a compound of the general formula

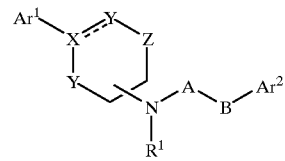

I wherein $Ar^1$ is phenyl, naphthyl or tetrahydronaphthyl, optionally substituted by hydroxy, lower alkoxy, nitro, amino or methanesulfonamide;

$Ar^2$ is phenyl, naphthyl or tetrahydronaphthyl, optionally substituted by lower alkyl or halogen;

X is C, CH, C(OH) or N;

Y is —$CH_2$—, CH or O;

Z —$CH_2$—, —$CH(CH_3)$— or —$C(CH_3)_2$—;

$R^1$ is hydrogen, lower alkyl or acetyl;

A is C=O or —$(CHR^2)_n$—, wherein $R^2$ is hydrogen, lower alkyl or hydroxy-lower alkyl;

B is —$(CH_2)_n$—, O, —$CH(OH)(CH_2)_n$—, —$CH(CH_2OH)(CH_2)_n$—, —$(CH_2)_n$ CH(OH)— or —CH($CH_2OH$)—;

- - - may be a bond; and n is 0–4, or pharmaceutically acceptable acid addition salts thereof.

14 Claims, No Drawings

METHOD OF TREATING A NEURODEGENERATIVE DISEASE BY ADMINISTERING AN ARYL-CYCLOHEXYLAMINE DERIVATIVE

FIELD OF THE INVENTION

The present invention relates to the treatment of neurodegenerative diseases.

BACKGROUND OF THE INVENTION

The present invention involves treatment with a compound of the general formula

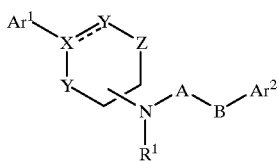

wherein
- $Ar^1$ is phenyl, naphthyl or tetrahydronaphthyl, optionally substituted by hydroxy, lower alkoxy, nitro, amino or methanesulfonamide;
- $Ar^2$ is phenyl, naphthyl or tetrahydronaphthyl, optionally substituted by lower alkyl or halogen;
- X is C, CH, C(OH) or N;
- Y is —$CH_2$—, CH or O
- Z —$CH_2$—, —$CH(CH_3)$— or —$C(CH_3)_2$—;
- $R^1$ is hydrogen, lower alkyl or acetyl;
- A is C=O or —$(CHR^2)_n$—, wherein $R^2$ is hydrogen, lower alkyl or hydroxy-lower alkyl;
- B is —$(CH_2)_n$—, O, —$CH(OH)(CH_2)_n$—, —$CH(CH_2OH)(CH_2)_n$—, —$(CH_2)_n CH(OH)$— or —$CH(CH_2OH)$—;
- - - - may be a bond and
- n is 0–4 and to pharmaceutically acceptable acid addition salts thereof.

Most of the described aryl derivatives are known compounds. In EP 503 411 and EP 481 299 are described N-phenyl-4-amino-piperidines with antiarrythmic and psychotropic activities. In WO 9715549 are described compounds of the present of formula I, which have a potent effect of stimulating beta-3 adrenaline receptors. These compounds were known to be useful for the treatment of urinary disorders such as frequent urination and urinary incontinence, convulsion and exasperation of the function of digestive tract movement, obesity and diabetes.

SUMMARY OF THE INVENTION

The present invention is a method of treatment of a neurodegenerative disease comprising administering a therapeutically effective amount of a compound of the general formula

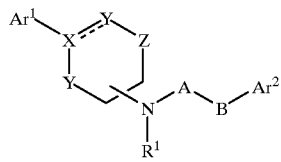

wherein
- $Ar^1$ is phenyl, naphthyl or tetrahydronaphthyl, optionally substituted by hydroxy, lower alkoxy, nitro, amino or methanesulfonamide;
- $Ar^2$ is phenyl, naphthyl or tetrahydronaphthyl, optionally substituted by lower alkyl or halogen;
- X is C, CH, C(OH) or N;
- Y is —$CH_2$—, CH or O;
- Z —$CH_2$—, —$CH(CH_3)$— or —$C(CH_3)_2$—;
- $R^1$ is hydrogen, lower alkyl or acetyl;
- A is C=O or —$(CHR^2)_n$—, wherein $R^2$ is hydrogen, lower alkyl or hydroxy-lower alkyl;
- B is —$(CH_2)_n$—, O, —$CH(OH)(CH_2)_n$—, —$CH(CH_2OH)(CH_2)_n$—, —$(CH_2)_n CH(OH)$— or —$CH(CH_2OH)$—;
- - - - may be a bond; and
- n is 0–4, or pharmaceutically acceptable acid addition salts thereof.

The diseases that may be treated in accordance with the present invention include stroke, brain trauma, Alzheimer's disease, Parkinson's disease, Huntington's disease, amyotrophic lateral sclerosis, neurodegeneration associated with bacterial sclerosis and neurodegeneration associated with bacterial or viral infection.

Moreover, the present invention relates to the method of treatment wherein the compound is administered in an amount from about 0.1 mg to about 1000 mg per day.

Detailed Description of the Invention It has now surprisingly been found that compounds of the present invention are NMDA(N-methyl-D-aspartate)-receptor subtype selective blockers, which have a key function in modulating neuronal activity and plasticity. These therepeutic properties make the compounds of formula I and their salts key players in mediating processes underlying development of CNS as well as learning and memory formation.

Under pathological conditions of acute and chronic forms of neurodegeneration, overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis), neurodegeneration associated with bacterial sclerosis and neurodegeneration associated with bacterial or viral infections.

In accordance with the present invention, the use of compounds of formula I and pharmaceutically acceptable acid addition salts thereof are administered in the treatment or prophylaxis of diseases, caused by overactivation of respective NMDA receptor subtype. Also encompassed by the present invention are methods of treatment by administering a compound of formula I or a pharmaceutically acceptable acid addition salt thereof or a pharmaceutical composition containing such compound.

The present invention embraces treatment with racemic mixtures and all their corresponding enantiomers of the compounds of formula I.

Referring to X as position 1 of the ring, the —N(R$^1$)—A—B—Ar$^2$ group can be a subsituent at ring position 2 (where 4 is not 0), 3 or 4.

The following definitions of the general terms used in the present description apply irrespective of whether the terms in question appear alone or in combination.

As used herein, the term "lower alkyl" denotes a straight- or branched-chain alkyl group containing from 1 to 4 carbon atoms, for example, methyl, ethyl, propyl, isopropyl, butyl and the like.

The term "halogen" denotes chlorine, iodine, fluorine and bromine.

The term "lower alkoxy" denotes a group wherein the alkyl residue is as defined above for "lower alkyl".

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "leaving group" has the meaning conventionally used, and refers to, for example, halogen, alkylsulfonyloxy, arylsulfonyloxy and the like. The most preferred leaving group in the present case is a halogen.

The compounds of the present invention may be subdivided in the following subgroups:

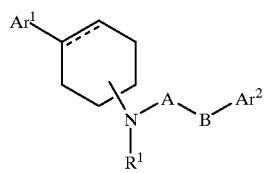

Ia

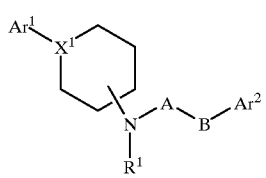

Ib

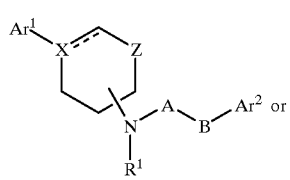

Ic

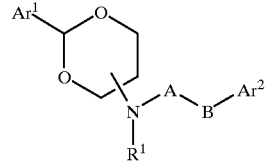

Id wherein Z is —CH(CH$_3$)— or C(CH$_3$)$_2$—, Ar$^1$, Ar$^2$, X, A, B, the dotted line and R$^1$ have the significances given above and X$^1$ is C(OH) or N.

Preferred compounds of formula Ia in the scope of the present invention are the following:

trans-4-[4-(3-phenyl-propylamino)-cyclohexyl]-phenol,
trans-4-[4-[methyl-(3-phenyl-propyl)-amino]-cyclohexyl]-phenol,
trans-4-[4-[ethyl-(3-phenyl-propyl)-amino]-cyclohexyl]-phenol,
trans-4-[4-(4-phenyl-butylamino)-cyclohexyl]-phenol,
trans-4-[4-[3-(4-fluoro-phenyl)-propylamino]-cyclohexyl] phenol,
trans-4-(4-[[3-(4-fluoro-phenyl)-propyl ]-methyl-amino]-cyclohexyl)-phenol,
trans-4-[4-[methyl-(2-p-tolyloxy-ethyl)-amino]-cyclohexyl]-phenol,
(RS)-4-[trans-4-(1-hydroxymethyl-3-phenyl-propylamino)-cyclohexyl]-phenol,
(RS)-4-[trans-4-(2-hydroxymethyl-3-phenyl-propylamino)-cyclohexyl]-phenol,
and
trans-N-(4-[4-[methyl-(3-phenyl-propyl)-amino]-cyclohexyl]-phenyl)-methanesulfonamide.

The following examples are preferred compounds of formula Ib:

cis-4-[1-hydroxy-4-(3-phenyl-propylamino)-cyclohexyl]-phenol,
4-[4-[methyl-(3-phenyl-propyl)-amino]-piperidin-1-yl]-phenol and
4-[4-(3-phenyl-propylamino)-piperidin-1-yl]-phenol.

A preferred compound of formula Ic is
(1RS, 3RS, 4RS)-4-[3-methyl-4-[methyl-(3-phenyl-propyl)-amino]-cyclohexyl]-phenol.

Further preferred is a compound of formula Id, which is
trans-4-[5-(3-phenyl-propylamino)-[1,3]dioxan-2-yl]-phenol.

The afore-mentioned compounds of formula I and their subgroups (Ia–Id) can be manufactured in accordance with known methods, for example by a) reacting a compound of formula

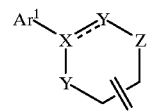

II with an amine of formula

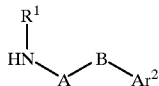
III wherein Ar¹, Ar², X, Y, Z, A, B and R¹ have the significances given above, or b) reacting a compound of formula

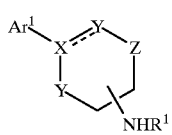
IV with a compound of formula

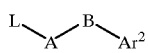
V wherein L is a leaving group and Ar¹, Ar², X, Y, Z, A, B and R¹ have the significances given above, or c) reacting a compound of formula

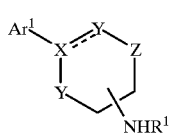
IV with a compound of formula

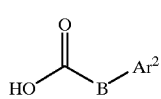
VI to give a compound of formula

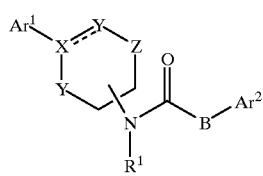
I-1 wherein Ar¹, Ar², X, Y, Z and B have the significances given above, or d) cleaving off an O-protecting group from a compound of formula

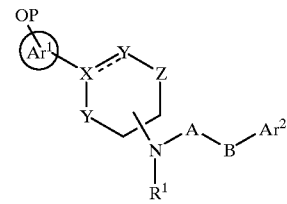
VII wherein Ar¹, Ar², X, Y, Z, R¹, A, B and R¹ have the significances given above and P is a protecting group, and, if desired, converting the compound of formula I obtained into a pharmaceutically acceptable salt.

Furthermore, a nitro group can be hydrogenated to an amino group, the amino group can be alkylated or converted into a group $NHSO_2CH_3$ by methods known in the art.

In accordance with reaction step a), a compound of formula II with an amine of formula III is heated in a Dean-Stark apparatus in a suitable solvent, such as toluene. A suitable amine is, for example, phenethylamine. The reduction of the imine intermediate is effected with a hydride donor in a suitable solvent, for example with borohydride in methanol.

In accordance with reaction variant b), a compound of formula IV is treated with a compound of formula V, wherein the most preferred leaving group is bromine. This reaction is carried out in conventional manner in the presence of $K_2CO_3$.

Process variant c) describes the reaction of a compound of formula IV with a corresponding acid derivative of formula VI. This reaction is carried out in the presence of CDI (carbonyl diimidazole) at 0° C. for about 1 h.

In accordance with process variant d), a compound of formula VII is deprotected to a compound of general formula I. Suitable protecting groups and methods for their cleavage will be familiar to any person skilled in the art, although of course there can be used only those protecting groups which can be cleaved off by methods under conditions of which other structural elements are not affected. The benzyl group is a preferred O-protecting group. The process is carried out in conventional manner. For example, a compound of formula VII is dissolved in a suitable solvent or mixture of solvents such as methanol, and hydrogenated.

Pharmaceutically acceptable salts can be manufactured according to methods which are known per se and familiar to any person skilled in the art. The acid addition salts of compounds of formula I are especially well suited for pharmaceutical use.

In schemes 1–7 are described processes for preparation of compounds of formula I, starting from known compounds or from compounds which can be prepared in conventional manner.

The starting materials of formulae II, III, VIII, IX, XII, XV, XVI, XVIII and IXX are commercial products or can be prepared according to methods known per se. The preparation of compounds of formula I are described in more detail in working examples 1–86.

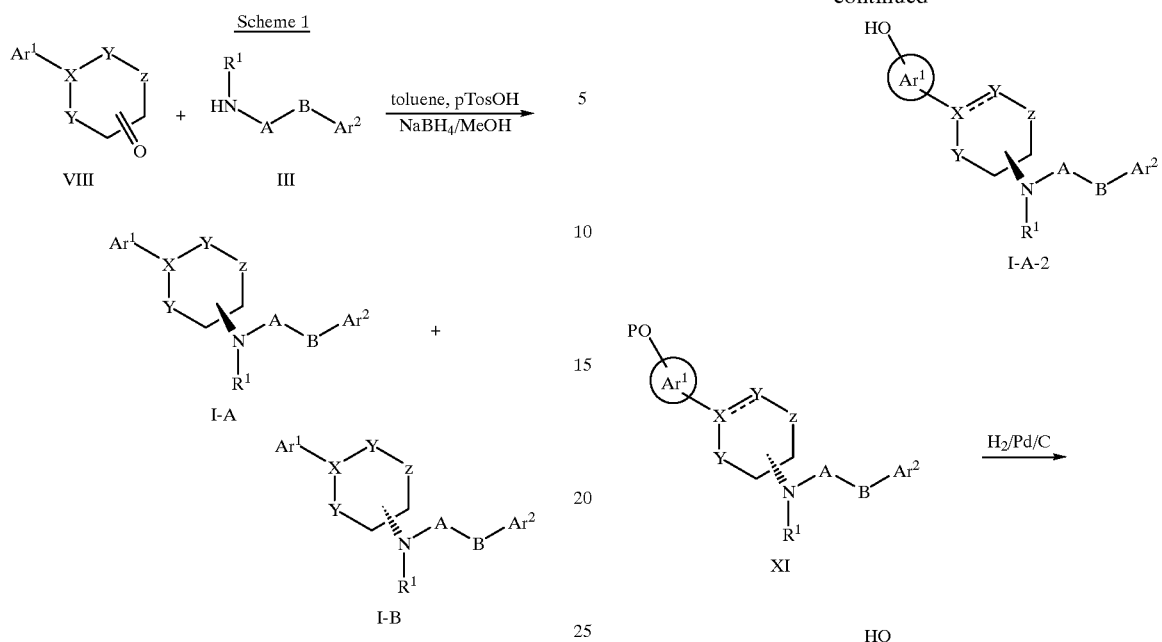
wherein the substituents are described as above.
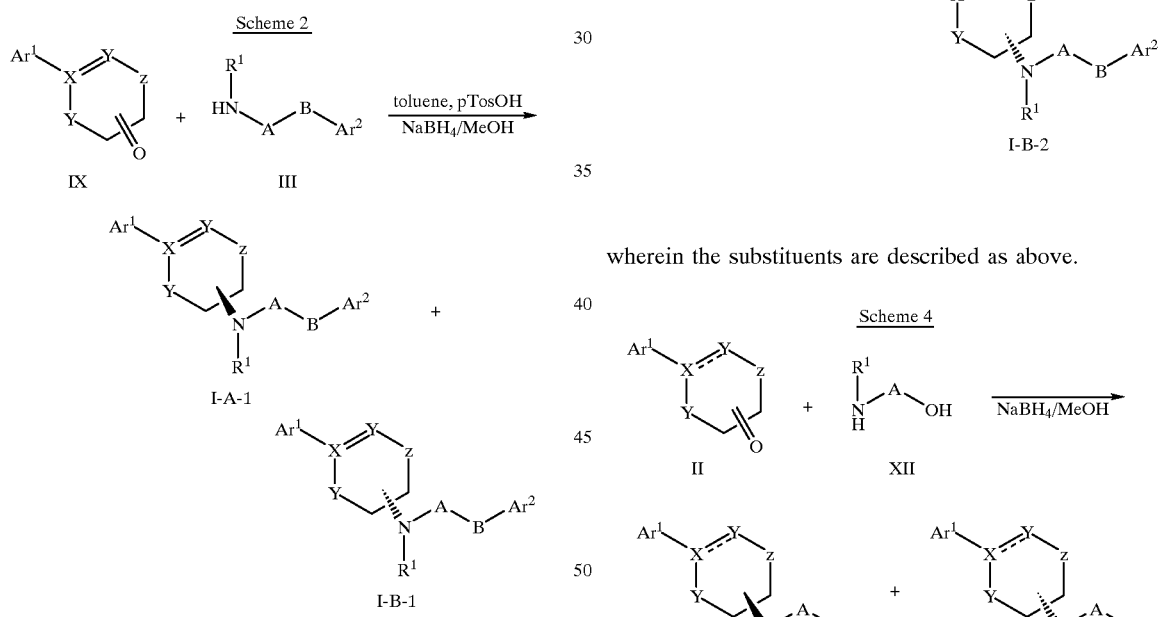
wherein the substituents are described as above.
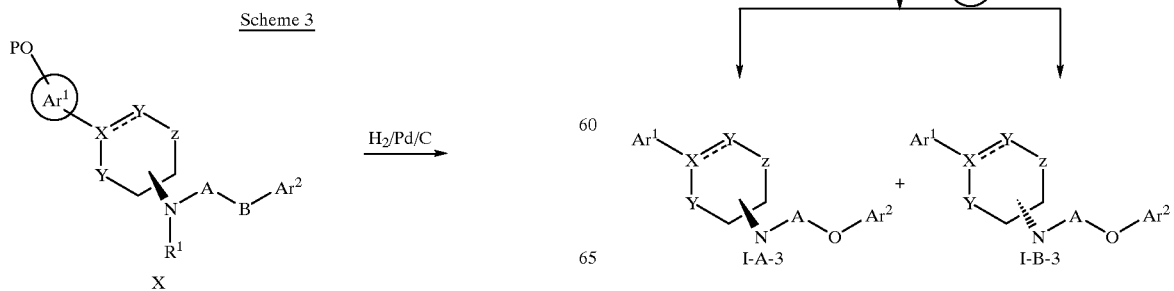

wherein the substituents are described as above.

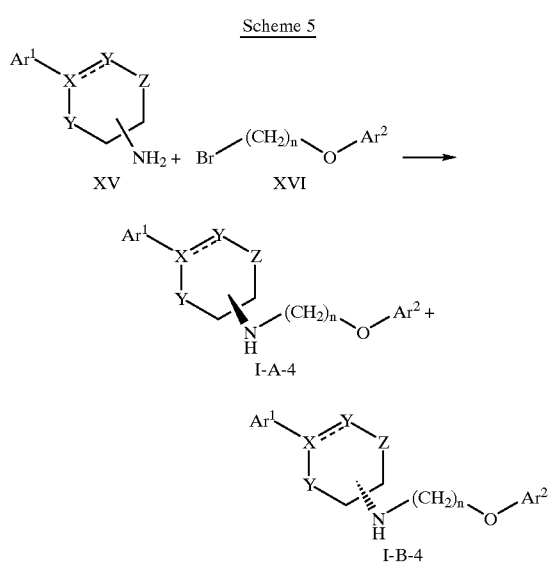

Scheme 5

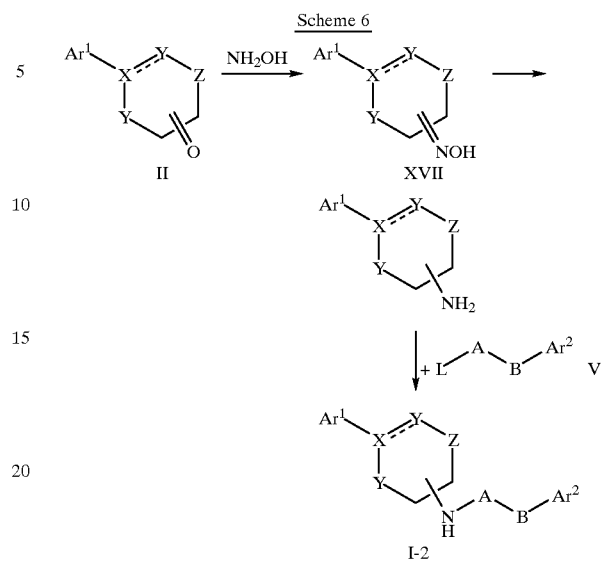

Scheme 6 wherein the substituents are described as above.

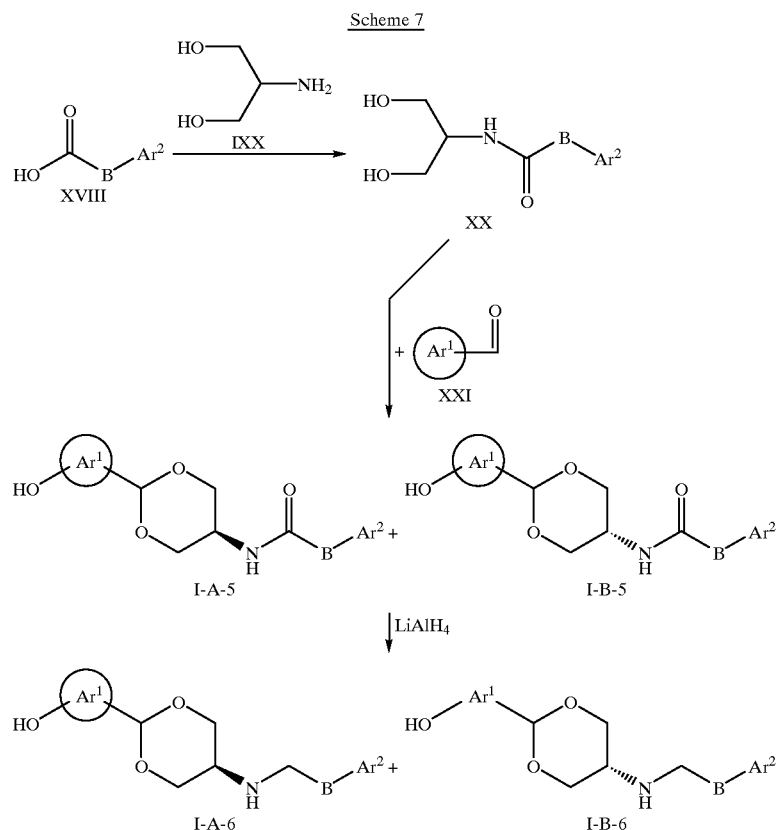

Scheme 7 wherein the substituents are described as above.

As mentioned earlier, the compounds of formula I and their pharmaceutically usable acid addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the test method as follows:.

Test Method

[R-(R*,S*)]-a-(4-Hydroxy-phenyl)-b-methyl-4-(phenyl-methyl)-1-piperidine propanol) Binding Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

Binding experiments were performed using a Tris-HCl 50 mM, pH 7.4 buffer. For displacement experiments 5 nM of [R-(R*,S*)]-a-(4-hydroxy-phenyl)-b-methyl-4-(phenyl-methyl)-1-piperidine propanol) were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zütrich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA). The $IC_{50}$ value refers to the concentration of a compound needed to give 50% inhibition, i.e., the concentration at which 50% of the ligands bonded to the receptor are displaced.

The $IC_{50}(\mu M)$ of preferred compounds tested in accordance with the above mentioned methods are in the range of about 0.004–0.01.

In the table below some data of active compounds are given:

| Example No. | $IC_{50}$ in $\mu M$ |
|---|---|
| 22b | 0.02 |
| 24 | 0.07 |
| 39b | 0.009 |
| 40c | 0.04 |
| 41b | 0.02 |
| 43b | 0.02 |
| 44b | 0.008 |
| 45b | 0.13 |
| 46b | 0.01 |

-continued

| Example No. | $IC_{50}$ in $\mu M$ |
|---|---|
| 47b | 0.03 |
| 48c | 0.04 |
| 50 | 0.08 |
| 56 | 0.011 |
| 57b | 0.01 |
| 58 | 0.04 |
| 60b | 0.007 |
| 61b | 0.004 |
| 62b | 0.006 |
| 63b | 0.02 |
| 64b | 0.06 |
| 65b | 0.01 |
| 66c | 0.02 |
| 67b | 0.1 |
| 70b | 0.1 |
| 71c | 0.025 |
| 73b | 0.01 |
| 74c | 0.01 |
| 75 | 0.007 |
| 77 | 0.007 |
| 81g | 0.027 |
| 83c | 0.06 |
| 85 | 0.022 |

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of from about 0.1 mg per day to about 1000 mg per day of a compound of general formula I, although the upper limit can also be exceeded when this is shown to be indicated. Oral dosage ranges are preferably from about 1 mg to about 500 mg per day. Most preferably, administration is in an amount from about 1 mg to about 100 mg daily. The preferred manner of administration is oral using a convenient dosage regime which is adjustable.

The following Examples illustrate the present invention in more detail. However, they are not intended to limit its scope in any manner. All temperatures are given in degrees celsius.

EXAMPLE 1

(1RS,2RS)-4-(2-Phenethylamino-cyclohexyl)-phenol

A 1M $BBr_3$—$CH_2Cl_2$ solution (9.4 ml, 9.4 mmol) was added to a solution of cis-[2-(4-methoxy-phenyl)-cyclohexyl]-phenethyl-amine (1.45 g, 4.69 mmol) in $CH_2Cl_2$ at 0°. After stirring for 2 h, the reaction mixture was poured on ice, treated with sat. $NaHCO_3$ solution and extracted with $CH_2Cl_2$. The residue was purified by chromatography over $SiO_2$ (Merck 230–400 mesh) eluting with $CH_2Cl_2$—MeOH—25% aq. $NH_3$ 140:10:1 to give after trituration with ether-hexane 570 mg of (1RS,2RS)-4-(2- phenethylamino-cyclohexyl)-phenol as a light brown powder. Mp. 121°, MS: m/e=296.3 (M+H$^+$).

EXAMPLE 2

(1RS,2SR)-4-(2-Phenethylamino-cyclohexyl)-phenol

Following the general method of example 1, (1RS,2SR)-[2-(4-methoxy-phenyl)-cyclohexyl]-phenethyl-amine (0.9 g, 2.9 mmol) was converted to (1RS,2SR)-4-(2-phenethylamino-cyclohexyl)-phenol, giving 0.63 g of a light brown powder. MS: m/e=296.3 (M+H$^+$).

EXAMPLE 3

(1RS,2RS)-[2-(4-Methoxy-phenyl)-cyclohexyl]-phenethyl-amine and (1RS,2SR)-[2-(4-Methoxy-phenyl)-cyclohexyl]-phenethyl-amine A mixture of 2-(4-methoxyphenyl)-cyclohexanone (prepared following the procedure described in W. E. Bachmann et al., J. Am. Chem. Soc., 1950, 72, 1995) (2.0 g, 9.79 mmol), phenethylamine (1.19 g, 9.79 mmol), toluene (40 ml) and a catalytical amount of p-toluenesulfonic acid was refluxed in a Dean-Stark apparatus overnight. After removal of the solvent, the residue was dissolved in MeOH (25 ml) and sodium borohydride (excess) was added. After stirring for 1 h at RT, the solvent was evaporated, H$_2$O was added to the residue. Extraction with CH$_2$Cl$_2$, drying of the organic layer over Na$_2$SO$_4$, evaporation of the solvent and chromatography of the residue over SiO$_2$ (Merck 230–400 mesh) eluting with AcOEt gave (1RS,2RS)-[2-(4-methoxy-phenyl)-cyclohexyl]-phenethyl-amine (1.5 g, 50%, light yellow oil, MS: m/e=310.2 (M+H$^+$)) and (1RS,2SR)-[2-(4-methoxy-phenyl)-cyclohexyl]-phenethyl-amine (0.95 g, 31%, light yellow oil, MS: m/e=310.2 (M+H$^+$)).

EXAMPLE 4

(1RS,2RS)-4-[2-(3-Phenyl-propylamino)-cyclohexyl]-phenol

Following the general method of example 1 (2RS,3RS)-[2-(4-methoxy-phenyl)-cyclohexyl]-(3-phenyl-propyl)-amine (0.4 g, 1.24 mmol) was converted to (1RS,2RS)-4-[2-(3-phenyl-propylamino)-cyclohexyl]-phenol, giving 0.27 g of a light yellow oil. MS: m/e=310.3 (M+H$^+$).

EXAMPLE 5

(1RS,2SR)-4-[2-(3-Phenyl-propylamino)-cyclohexyl]-phenol

Following the general method of example 1 (2RS,3SR)-[2-(4-methoxy-phenyl)-cyclohexyl]-(3-phenyl-propyl)-amine (0.28 g, 0.87 mmol) was converted to (1RS,2SR)-4-[2-(3-phenyl-propylamino)-cyclohexyl]-phenol, giving 0.17 g of a light brown solid. MS: m/e=310.3 (M+H$^+$).

EXAMPLE 6

(2RS,3RS)-[2-(4-Methoxy-phenyl)-cyclohexyl]-(3-phenyl-propyl)-amine and (2RS,3SR)-[2-(4-Methoxy-phenyl)-cyclohexyl]-(3-phenyl-propyl)-amine Following the general method of example 3 (2RS,3RS)-[2-(4-methoxy-phenyl)-cyclohexyl]-(3-phenyl-propyl)-amine (510 mg; 16%), colorless oil, MS: m/e=324.4 (M+H$^+$)) and (2RS,3SR)-[2-(4-methoxy-phenyl)-cyclohexyl]-(3-phenyl-propyl)-amine (310 mg; 10%) colorless oil, MS: m/e=324.4 (M+H$^+$)) were prepared from 2-(4-methoxyphenyl)-cyclohexanone (2.0 g; 9.8 mmol) and 3-phenylpropylamine (1.32 g; 9.8 mmol).

EXAMPLE 7

(1RS,2RS)-4-[2-(4-Phenyl-butylamino)-cyclohexyl]-phenol

Following the general method of example 1 (2RS,3RS)-[2-(4-methoxy-phenyl)-cyclohexyl]-(3-phenyl-butyl)-amine (1.75 g, 5.19 mmol) was converted to (1RS,2RS)-4-[2-(3-phenyl-butylamino)-cyclohexyl]-phenol, giving 0.50 g of a white solid. MS: m/e=324.3 (M+H$^+$).

EXAMPLE 8

(1RS,2SR)-4-[2-(4-Phenyl-butylamino)-cyclohexyl]-phenol

Following the general method of example 1 (2RS,3SR)-[2-(4-methoxy-phenyl)-cyclohexyl]-(3-phenyl-butyl)-amine (0.95 g, 2.81 mmol) was converted to (1RS,2SR)-4-[2-(3-phenyl-butylamino)-cyclohexyl]-phenol, giving 0.45 g of a light brown solid. MS: m/e=324.3 (M+H$^+$).

EXAMPLE 9

(1RS,2RS)-[2-(4-Methoxy-phenyl)-cyclohexy]-(4-phenyl-butyl)-amine and (1RS,2SR)-[2-(4-Methoxy-phenyl)-cyclohexyl]-(4-phenyl-butyl)-amine Following the general method of example 3 (2RS,3RS)-[2-(4-methoxy-phenyl)-cyclohexyl]-(3-phenyl-butyl)-amine (1.8 g; 54%) light yellow oil, MS: m/e=338.3 (M+H$^+$)) and (2RS,3SR)-[2-(4-methoxy-phenyl)-cyclohexyl]-(3-phenyl-butyl)-amine (1.0 g; 30% light yellow oil, MS: m/e=338.3 (M+H$^+$)) were prepared from 2-(4-methoxyphenyl)-cyclohexanone(2.0 g; 9.8 mmol) and 4-phenylbutylamine (1.46 g; 9.8 mmol).

EXAMPLE 10

(1RS,2RS)-3-(2-Phenethylamino-cyclohexyl)-phenol (1RS,2RS)-[2-(3-methoxy-phenyl)-cyclohexyl]-phenethyl-amine hydrochloride (1:1) (0.7 g, 2.26 mmol) was first treated with NaHCO$_3$ and then, following the general method of example 1, was converted to (1RS,2RS)-3-(2-phenethylamino-cyclohexyl)-phenol, giving 0.51 g of a light brown powder. MS: m/e=296.3 (M+H$^+$).

EXAMPLE 11

(1RS, 2SR)-3-(2-Phenethylamino-cyclohexyl)-phenol

Following the general method of example 1, (1RS,2SR)-[2-(3-methoxy-phenyl)-cyclohexyl]-phenethyl-amine (1.7 g, 5.49 mmol) was converted to (1RS,2SR)-3-(2-phenethylamino-cyclohexyl)-phenol, giving 1.04 g of white crystalline material. Mp. 164–165°, MS: m/e=296.3 (M+H$^+$).

EXAMPLE 12

(1RS,2RS)-[2-(3-Methoxy-phenyl)-cyclohexyl]-phenethyl-amine hydrochloride (1:1) and (1RS, 2SR)-[2-(3-Methoxy-phenyl)-cyclohexyl]-phenethyl-amine Following the general method of example 3 (2RS,3RS)-[2-(4-methoxy-phenyl)-cyclohexyl]-phenetyl-amine (of which the hydrochloride salt was prepared with HCl in Ether: 1.3 g; 15% light brown solid, MS: m/e=310.2 (M+H$^+$)) and (2RS,3SR)-[2-(4-methoxy-phenyl)-cyclohexyl]-phenetyl-amine (1.7 g; 22% light yellow oil, MS: m/e=310.2 (M+H$^+$)) were prepared from 2-(3-methoxyphenyl)-cyclohexanone (5.0 g; 24.5 mmol) and phenethylamine (2.97 g; 24.5 mmol).

EXAMPLE 13

(1RS,2RS)-3-[2-(3-Phenyl-propylamino)-cyclohexyl]-phenol

Following the general method of example 1, (1RS,2RS)-[2-(3-methoxy-phenyl)-cyclohexyl]-(3-phenyl-propyl)-amine (1.6 g, 4.95 mmol) was converted to (1RS,2RS)-3-[2-(3-phenyl-propylamino)-cyclohexyl]-phenol, giving 0.85 g of a white crystalline material. Mp. 112–113°, MS: m/e= 310.2 (M+H$^+$).

EXAMPLE 14

(1RS,2SR)-3-[2-(3-Phenyl-propylamino)-cyclohexyl]-phenol

Following the general method of example 1, (1RS,2SR)-[2-(3-methoxy-phenyl)-cyclohexyl]-(3-phenyl-propyl)-amine (1.2 g, 3.71 mmol) was converted to (1RS,2SR)-3-[2-(3-phenyl-propylamino)-cyclohexyl]-phenol, giving 0.65 g of a white crystalline material. Mp. 112–113°, MS: m/e= 310.2 (M+H$^+$).

EXAMPLE 15

(1RS,2RS)-[2-(3-Methoxy-phenyl)-cyclohexyl]-(3-phenyl-propyl)-amine and (1RS,2SR)-[2-(3-Methoxy-phenyl)-cyclohexyl]-(3-phenyl-propyl)-amine Following the general method of example 3 (2RS,3RS)-[2-(3-methoxy-phenyl)-cyclohexyl]-(3-phenyl-propyl)-amine (1.63 g; 21% light yellow oil, MS: m/e=324.4 (M+H$^+$)) and (2RS,3SR)-[2-(3-methoxy-phenyl)-cyclohexyl]-(3-phenyl-propyl)-amine (1.28 g; 16% light yellow oil, MS: m/e=324.4 (M+H$^+$)) were prepared from 2-(3-methoxyphenyl)-cyclohexanone (5.0 g; 24.5 mmol) and 3-phenylpropylamine(3.31 g; 24.5 mmol).

EXAMPLE 16

(1RS,2RS)-3-[2-(4-Phenyl-butylamino)-cyclohexyl]-phenol

Following the general method of example 1, (1RS,2RS)-[2-(3-methoxy-phenyl)-cyclohexyl]-(4-phenyl-butyl)-amine (1.6 g, 4.95 mmol) was converted to (1RS,2RS)-3-[2-(4-phenyl-butylamino)-cyclohexyl]-phenol, giving 0.64 g of a light brown crystalline material. Mp. 115–116°, MS: m/e= 324.3 (M+H$^+$).

EXAMPLE 17

(1RS,2SR)-3-[2-(4-Phenyl-butylamino)-cyclohexyl]-phenol

Following the general method of example 1, (1RS,2SR)-[2-(3-methoxy-phenyl)-cyclohexyl]-(4-phenyl-butyl)-amine (1.6 g, 4.95 mmol) was converted to (1RS,2SR)-3-[2-(4-phenyl-butylamino)-cyclohexyl]-phenol, giving 0.98 g of a light brown crystalline material. Mp. 131–132°, MS: m/e= 324.3 (M+H$^+$).

EXAMPLE 18

(1RS,2RS)-[2-(3-Methoxy-phenyl)-cyclohexyl]-(4-phenyl-butyl)-aminehydrochloride (1:1) and (1RS, 2SR)-[2-(3-Methoxy-phenyl)-cyclohexyl]-(4-phenyl-butyl)-amine Following the general method of example 3 (2RS,3RS)-[2-(3-methoxy-phenyl)-cyclohexyl]-(4-phenyl-butyl)-amine (of which the hydrochloride salt was prepared with HCl in Ether, 1.8 g; 20% light brown solid, MS: m/e=338.2 (M+H$^+$)) and (2RS,3SR)-[2-(3-methoxy-phenyl)-cyclohexyl]-(4-phenyl-butyl)-amine (1.6 g; 19% light yellow oil, MS: m/e=338.2 (M+H$^+$)) were prepared from 2-(3-methoxyphenyl)-cyclohexanone(5.0 g; 24.5 mmol) and 4-phenylbutylamine (3.65 g; 24.5 mmol).

EXAMPLE 19 cis-4-(4-Phenethylamino-cyclohexyl)-phenol

Following the general method of example 22b, cis-[4-(4-benzyloxy-phenyl)-cyclohexyl]-phenethyl-amine (140 mg) was hydrogenated to give cis-4-(4-phenethylamino-cyclohexyl)-phenol as white crystals (52 mg; 49%). MS: m/e=296.4 (M+H$^+$).

EXAMPLE 20 trans-4-(4-Phenethylamino-cyclohexyl)-phenol a) cis-[4-(4-Benzyloxy-phenyl)-cyclohexyl]-phenethyl-amine and trans-[4-(4-Benzyloxy-phenyl)-cyclohexyl]-phenethyl-amine Following the general method of example 3, cis-[4-(4-benzyloxy-phenyl)-cyclohexyl]-phenethyl-amine, (260 mg; 11% light yellow oil, MS: m/e=386.2 (M+H$^+$)) trans-[4-(4-benzyloxy-phenyl)-cyclohexyl]-phenethyl-amine (370 mg; 15 % white crystals, MS: m/e=386.3 (M+H$^+$)) were prepared from 4-(4-benzyloxy-phenyl)-cyclohexanone (1.8 g; 6.4 mmol) and phenetylamine (0.78 g; 6.4 mmol).

b) trans-4-(4-Phenethylamino-cyclohexyl)-phenol

Following the general method of 22b, trans-[4-(4-benzyloxy-phenyl)-cyclohexyl]-phenethyl-amine (190 mg) was hydrogenated to give trans-4-(4-phenethylamino-cyclohexyl)-phenol as white crystals (125 mg; 86%). MS: m/e=296.4 (M+H$^+$).

EXAMPLE 21 cis-4-[4-(3-Phenyl-propylamino)-cyclohexyl]-phenol hydrochloride (1:1)

Following the general method of 22b, cis-[4-(4-benzyloxy-phenyl)-cyclohexyl]-(3-phenyl-propyl)-amine (200 mg; 0.5 mmol) was hydrogenated to give cis-4-[4-(3-phenyl-propylamino)-cyclohexyl]-phenol. The hydrochloride salt was prepared with HCl in ether to give white crystals (145 mg; 84%). MS: m/e=310.2 (M+H$^+$).

EXAMPLE 22 trans-4-[4-(3-Phenyl-propylamino)-cyclohexyl]-phenol a) cis-[4-(4-Benzyloxy-phenyl)-cyclohexyl]-(3-phenyl-propyl)-amine and trans-[4-(4-Benzyloxy-phenyl)-cyclohexyl]-(3-phenyl-propyl)-amine Following the general method of example 3, cis-[4-(4-benzyloxy-phenyl)-cyclohexyl]-(3-phenyl-propyl)-amine, (710 mg; 17% light yellow oil, MS: m/e=400.4 (M+H$^+$)) trans-[4-(4-benzyloxy-phenyl)-cyclohexyl]-(3-phenyl-propyl)-amine (1.26 g; 30% white crystals, MS: m/e=400.4 (M+H$^+$)) were prepared from 4-(4-benzyloxy-phenyl)-cyclohexanone (3.0 g; 10.7 mmol) and 3-phenyl-propylamine(1.45 g; 10.7 mmol).

b) trans-4-[4-(3-Phenyl-propylamino)-cyclohexyl]-phenol

A mixture of trans-[4-(4-benzyloxy-phenyl)-cyclohexyl]-(3-phenyl-propyl)-amine (200 mg, 0.5 mmol), Pd/C 10% (20 mg) and MeOH (20 ml) was hydrogenated at RT for 3 h. Removal of the catalyst and evaporation of the solvent left a residue which after trituration with ether gave trans-4-[4-(3-phenyl-propylamino)-cyclohexyl]-phenol (130 mg, 84%) as a white crystalline material. MS: m/e=310.3 (M+H$^+$).

EXAMPLE 23 cis-4-[4-(4-Phenyl-butylamino)-cyclohexyl]-phenol hydrochloride (1:1)

a) cis-[4-(4-Benzyloxy-phenyl)-cyclohexy]-(4-phenyl-butyl)-amine and trans-[4-(4-Benzyloxy-phenyl)-cyclohexyl]-(4-phenyl-butyl)-amine Following the general method of example 3, cis-[4-(4-benzyloxy-phenyl)-cyclohexyl]-(4-phenyl-butyl)-amine, (780 mg; 18% light yellow oil, MS: m/e=414.4 (M+H$^+$)) trans-[4-(4-benzyloxy-phenyl)-cyclohexyl]-(4-phenyl-butpyl)-amine (1.25 g; 28% white crystals, MS: m/e=414.4 (M+H$^+$)) were prepared from 4-(4-benzyloxy-phenyl)-cyclohexanone (3.0 g; 10.7 mmol) and 4-phenyl-butylamine (1.6 g; 10.7 mmol).

b) cis-4-[4-(4-Phenyl-butylamino)-cyclohexyl]-phenol hydrochloride (1:1)

Following the general method of example 22b, cis-[4-(4-benzyloxy-phenyl)-cyclohexyl]-(4-phenyl-butyl)-amine (200 mg; 0.48 mmol) was hydrogenated to give cis-4-[4-(4-phenyl-butylamino)-cyclohexyl]-phenol. The hydrochloride salt was prepared with HCl in ether to give white crystals (140 mg; 80%). MS: m/e=324.4 (M+H$^+$).

EXAMPLE 24 trans-4-[4-(4-Phenyl-butylamino)-cyclohexyl]-phenol

Following the general method of example 22b, trans-[4-(4-benzyloxy-phenyl)-cyclohexyl]-(4-phenyl-butyl)-amine (200 mg) was hydrogenated to give trans-4-[4-(4-phenyl-butylamino)-cyclohexyl]-phenol as white crystals (150 mg; 96%). MS: m/e=324.3 (M+H$^+$).

EXAMPLE 25

(1RS,3SR)-4-(3-Phenethylamino-cyclohexyl)-phenol

Following the general method of example 1, (1RS,3SR)-[3-(4-methoxy-phenyl)-cyclohexyl]-phenethyl-amine (0.565 g, 1.83 mmol) was converted to (1RS,3SR)-4-(3-phenethylamino-cyclohexyl)-phenol (0.15 g, 28%, white solid, MS: m/e=296.4 (M+H$^+$)).

EXAMPLE 26

(1RS,3RS)-4-(3-Phenethylamino-cyclohexyl)-phenol

Following the general method of example 1, (1RS,3RS)-[3-(4-methoxy-phenyl)-cyclohexyl]-phenethyl-amine (0.23 g, 0.74 mmol) was converted to (1RS,3RS)-4-(3-phenethylamino-cyclohexyl)-phenol (0.13 g, 59%, light yellow solid, MS: m/e=296.4 (M+H$^+$)).

EXAMPLE 27

(1RS,3SR)-[3-(4-Methoxy-phenyl)-cyclohexyl]-phenethyl-amine and (1RS,3RS)-[3-(4-Methoxy-phenyl)-cyclohexyl]-phenethyl-amine A mixture of (RS)-[3-(4-methoxy-phenyl)-cyclohex-2-enyl]-phenethyl-amine (1.5 g, 4.88 mmol), 10% Pd/C (0.3 g) and MeOH (30 ml) was hydrogenated for 3 h. Removal of the catalyst, evaporation of the solvent and separation of the isomers by flash-chromatography over SiO$_2$ (Biotage 40, 90 g) eluting with AcOEt gave (1RS,3SR)-[3-(4-methoxy-phenyl)-cyclohexyl]-phenethyl-amine (0.57 g, 38%, light yellow oil, MS: m/e=310.2 (M+H$^+$)) and (1RS,3RS)-[3-(4-methoxy-phenyl)-cyclohexyl]-phenethyl-amine (0.25 g, 17%, light yellow oil, MS: m/e=310.2 (M+H$^+$)).

EXAMPLE 28

(RS)-[3-(4-Methoxy-phenyl)-cyclohex-2-enyl]-phenethyl-amine

A mixture of 3-(4-methoxy-phenyl)-cyclohex-2-enone (prepared following the procedure described in CA:54-10947d) (2.0 g, 9.89 mmol), phenethylamine (1.20 g, 9.89 mmol), toluene (50 ml) and a catalytical amount of p-toluenesulfonic acid was refluxed in a Dean-Stark apparatus overnight. After removal of the solvent, the residue was dissolved in MeOH (30 ml) and sodium borohydride (excess) was added. After stirring for 1 h at RT, the solvent was evaporated, H$_2$O was added to the residue. Extraction with CH$_2$Cl$_2$, drying of the organic layer over Na$_2$SO$_4$, evaporation of the solvent and flash-chromatography of the residue over SiO$_2$ (Biotage-40, 90 g) eluting with CH$_2$Cl$_2$—MeOH 95:5 gave (RS)-[3-(4-methoxy-phenyl)-cyclohex-2-enyl]-phenethyl-amine (1.7 g, 56%, light yellow solid, MS: m/e=308.2 (M+H$^+$)).

EXAMPLE 29

(RS)-4-(3-Phenethylamino-cyclohex-1-enyl)-phenol

Following the general method of example 1 (RS)-[3-(4-methoxy-phenyl)-cyclohex-2-enyl]-phenethyl-amine (0.15 g, 0.49 mmol) was converted to (RS)-4-(3-phenethylamino-cyclohex-1-enyl)-phenol, giving 0.04 g of a light yellow solid. MS: m/e=294.3 (M+H$^+$).

EXAMPLE 30

(1RS,3SR)-4-[3-(3-Phenyl-propylamino)-cyclohexyl]-phenol

Following the general method of example 1, (1RS,3SR)-[3-(4-methoxy-phenyl)-cyclohexy]-(3-phenyl-propyl)-amine (0.635 g, 1.96 mmol) was converted to (1RS,3SR)-4-[3-(3-phenyl-propylamino)-cyclohexyl]-phenol (0.3 g, 49%, light yellow oil, MS: m/e=310.2 (M+H$^+$)).

EXAMPLE 31

(1RS,3RS)-4-[3-(3-Phenyl-propylamino)-cyclohexyl]-phenol

Following the general method of example 1, (1RS,3RS)-[3-(4-methoxy-phenyl)-cyclohexyl]-(3-phenyl-propyl)- amine (0.31 g, 0.96 mmol) was converted to (1RS,3RS)-4-[3-(3-phenyl-propylamino)-cyclohexy]-phenol (0.15 g, 51%, light yellow oil, MS: m/e=310.3 (M+H$^+$)).

EXAMPLE 32

(1RS,3SR)-[3-(4-Methoxy-phenyl)-cyclohexyl]-(3-phenyl-propyl)-amine and (1RS,3RS)-[3-(4-Methoxy-phenyl)-cyclohexyl]-(3-phenyl-propyl)-amine A mixture of (RS)-[3-(4-methoxy-phenyl)-cyclohex-2-enyl]-(3-phenyl-propyl)-amine (1.54 g, 4.79 mmol), 10% Pd/C (0.3 g) and MeOH (30 ml) was hydrogenated for 3 h. Removal of the catalyst, evaporation of the solvent and separation of the isomers by flash-chromatography over SiO$_2$ (Biotage 40, 90 g) eluting with AcOEt gave (1RS,3SR)-[3-(4-methoxy-phenyl)-cyclohexyl]-(3-phenyl-propyl)-amine (0.64 g, 41%, light yellow oil, MS: m/e=324.4 (M+H$^+$)) and (1RS,3RS)-[3-(4-methoxy-phenyl)-cyclohexyl]-(3-phenyl-propyl)-amine (0.34 g, 22%, light yellow oil, MS: m/e=324.4 (M+H$^+$)).

EXAMPLE 33

(RS)-[3-(4-Methoxy-phenyl)-cyclohex-2-enyl]-(3-phenyl-propyl)-amine

Following the general procedure of example 28, (RS)-[3-(4-methoxy-phenyl)-cyclohex-2-enyl]-(3-phenyl-propyl)-amine (1.9 g; 40% light yellow oil, MS: m/e=322.3 (M+H$^+$)) was prepared from 3-(4-methoxy-phenyl)-cyclohex-2-enone (3.0 g; 14.8 mmol) and 3-phenyl-propylamine (2.0 g; 14.8 mmol).

EXAMPLE 34

(RS)-4-[3-(3-Phenyl-propylamino)-cyclohex-1-enyl]-phenol

Following the general method of example 1 (RS)-[3-(4-methoxy-phenyl)-cyclohex-2-enyl]-(3-phenyl-propyl)-amine (0.20 g, 0.62 mmol) was converted to (RS)-4-[3-(3-phenyl-propylamino)-cyclohex-1-enyl]-phenol, giving 0.06 g of a light yellow oil. MS: m/e=308.3 (M+H$^+$).

EXAMPLE 35

(1RS,3SR)-4-[3-(4-Phenyl-butylamino)-cyclohexyl]-phenol

Following the general method of example 1, (1RS,3SR)-[3-(4-methoxy-phenyl)-cyclohexyl]-(4-phenyl-butyl)-amine (1.1 g, 3.26 mmol) was converted to (1RS,3SR)-4-[3-(4-phenyl-butylamino)-cyclohexyl]-phenol (0.7 g, 66%, light yellow oil, MS: m/e=324.4 (M+H$^+$)).

EXAMPLE 36

(1RS,3RS)-4-[3-(4-Phenyl-butylamino)-cyclohexyl]-phenol

Following the general method of example 1, (1RS,3RS)-[3-(4-methoxy-phenyl)-cyclohexyl]-(4-phenyl-butyl)-amine (0.4 g, 1.19 mmol) was converted to (1RS,3RS)-4-[3-(4-phenyl-butylamino)-cyclohexyl]-phenol (0.16 g, 42%, light yellow oil, MS: m/e=324.4 (M+H$^+$)).

EXAMPLE 37

(1RS,3SR)-[3-(4-Methoxy-phenyl)-cyclohexyl]-(4-phenyl-butyl)-amine and (1RS ,3RS)-[3-(4-Methoxy-phenyl)-cyclohexyl]-(4-phenyl-butyl)-amine A mixture of (RS)-[3-(4-methoxy-phenyl)-cyclohex-2-enyl]-(4-phenyl-butyl)-amine (2.4 g, 7.15 mmol), 10% Pd/C (0.48 g) and MeOH (50 ml) was hydrogenated for 3 h. Removal of the catalyst, evaporation of the solvent and separation of the isomers by flash-chromatography over SiO$_2$ (Biotage 40, 90 g) eluting with AcOEt gave (1RS,3SR)-[3-(4-methoxy-phenyl)-cyclohexyl]-(4-phenyl-butyl)-amine (1.2 g, 50%, light yellow oil, MS: m/e=338.3 (M+H$^+$)) and (1RS,3RS)-[3-(4-methoxy-phenyl)-cyclohexl]-4-phenyl-butyl)-amine (0.43 g, 18%, light yellow oil, MS: m/e=338.3 (M+H$^+$)).

EXAMPLE 38

(RS)-[3-(4-Methoxy-phenyl)-cyclohex-2-enyl]-(4-phenyl-butyl)-amine

Following the general procedure of example 28, (RS)-[3-(4-methoxy-phenyl)-cyclohex-2-enyl]-(3-phenyl-butyl)-amine (2.8 g; 56% light yellow oil, MS: m/e=336.2 (M+H$^+$)) was prepared from 3-(4-methoxy-phenyl)-cyclohex-2-enone (3.0 g; 14.8 mmol) and 4-phenyl-butylamine (2.21 g; 14.8 mmol).

EXAMPLE 39 trans-4-{4-[Methyl-(3-phenyl-propyl)-amino]-cyclohexyl}-phenol a) trans-[4-(4-Benzyloxy-phenyl)-cyclohexyl]-methyl-(3-phenyl-propyl)-amine A mixture of trans-[4-(4-benzyloxy-phenyl)-cyclohexyl]-(3-phenyl-propyl)-amine (0.4 g, 1.0 mmol), 36.5% aq. formaldehyde (0.12 ml) and MeOH (7 ml) was stirred overnight at RT. Excess sodium borohydride was then added, and stirring was continued for 2 h. Evaporation of the solvent, addition of H$_2$O, extraction with CH$_2$Cl$_2$, drying of the organic layer with Na$_2$SO$_4$, evaporation of the solvent and purification of the residue by chromatography over SiO$_2$ (Merck 230–400 mesh) eluting with CH$_2$Cl$_2$—MeOH—25% aq. NH$_3$ 140:10:1 trans-[4-(4-benzyloxy-phenyl)-cyclohexyl]-methyl-(3-phenyl-propyl)-amine (0.41 g, 99%) as a colorless oil. MS: m/e=413 (M$^+$).

b) trans-4-{4-[Methyl-(3-phenyl-propyl)-amino]-cyclohexyl}-phenol

Following the general method of example 22b, trans-[4-(4-benzyloxy-phenyl)-cyclohexyl]-methyl-(3-phenyl-propyl)-amine (400 mg; 0.97 mmol) was hydrogenated to give trans-4-{4-[Methyl-(3-phenyl-propyl)-amino]-cyclohexyl}-phenol (173 mg; 55%) as white crystals. Mp. 156–158°, MS: m/e=324.4 (M+H$^+$).

EXAMPLE 40 trans-4-{4-[Ethyl-(3-phenyl-propyl)-amino]-cyclohexyl}-phenol a) trans-N-[4-(4-Benzyloxy-phenyl)-cyclohexyl]-N-(3-phenyl-propyl)-acetamide A mixture of trans-[4-(4-benzyloxy-phenyl)-cyclohexyl]-(3-phenyl-propyl)-amine (0.4 g, 1.0 mmol), pyridine (4 ml) and acetic anhydride (2 ml) was stirred at 0° for 1 h. Evaporation of the solvents and crystallization of the residue with hexane, gave trans-N-[4-(4-benzyloxy-phenyl)-cyclohexyl]-N-(3-phenyl-propyl)-acetamide (0.26 g, 59%) as white crystals. Mp. 80.0–81.5°, MS: m/e=441 (M$^+$).

b) trans-[4-(4-Benzyloxy-phenyl)-cyclohexyl]-ethyl-(3-phenyl-propyl)-amine

To a mixture of LiAlH$_4$ (74 mg, 1.95 mmol) and THF (10 ml) at 0° under Argon, a solution of trans-N-[4-(4- benzyloxy-phenyl)-cyclohexyl]-N-(3-phenyl-propyl)-acetamide (0.43 g, 0.97 mmol) in THF (10 ml) was added. The suspension was stirred for 2 h at RT and for 1 h at reflux. After cooling to 0°, $H_2O$ (0.4 ml) was carefully added, followed by 15% NaOH (0.4 ml) and $H_2O$ (0.4 ml). The precipitate was removed by filtration and the filtrate dried over $Na_2SO_4$, and evaporated. The residue was purified by chromatography over $SiO_2$ (Merck 230–400 mesh) eluting with $CH_2Cl_2$—MeOH 95:5 to give trans-[4-(4-benzyloxy-phenyl)-cyclohexyl]-ethyl-(3-phenyl-propyl)-amine (0.11 g, 26%) as a colorless oil. MS: m/e=328.5 (M+H$^+$).

c) trans-4-{4-[Ethyl-(3-phenyl-propyl)-amino]-cyclohexyl}-phenol

Following the general method of example 22b, 100 mg trans-[4-(4-benzyloxy-phenyl)-cyclohexyl]-ethyl-(3-phenyl-propyl)-amine was hydrogenated to trans-4-{4-[ethyl-(3-phenyl-propyl)-amino]-cyclohexyl}-phenol (16 mg; 20%) as white crystals. Mp. 163–166°, MS: m/e=338.3 (M+H$^+$).

EXAMPLE 41 trans-4-{4-[Methyl-(2-phenoxy-ethyl)-amino]-cyclohexyl}-phenol a) trans-[4-(4-Benzyloxy-phenyl)-cyclohexyl]-methyl-(2-phenoxy-ethyl)-amine Following the general method of example 39a, trans-[4-(4-benzyloxy-phenyl)-cyclohexyl]-(2-phenoxy-ethyl)-amine (300 mg) was N-methylated to give trans-[4-(4-benzyloxy-phenyl)-cyclohexyl]-methyl-(2-phenoxy-ethyl)-amine (296 mg; 95%) as light yellow crystals. Mp. 67–69°, MS: m/e=316.3 (M+H$^+$).

b) trans-4-{4-[Methyl-(2-phenoxy-ethyl)-amino]-cyclohexyl}-phenol

Following the general method of example 22b, trans-[4-(4-benzyloxy-phenyl)-cyclohexyl]-methyl-(2-phenoxy-ethyl)-amine (200 mg) was hydrogenated to give trans-4-{4-[methyl-(2-phenoxy-ethyl)-amino]-cyclohexyl}-phenol (83 mg; 53%) as white crystals. Mp. 90–92°, MS: m/e=326.3 (M+H$^+$).

EXAMPLE 42 cis-4-[4-(2-Phenoxy-ethylamino)-cyclohexyl]-phenol

Following the general method of example 22b, cis-[4-(4-benzyloxy-phenyl)-cyclohexyl]-(2-phenoxy-ethyl)-amine (120 mg) was hydrogenated to give cis-4-[4-(2-phenoxy-ethylamino)-cyclohexyl]-phenol (69 mg; 92%) as light yellow crystals. Mp. 149–154°, MS: m/e=312.2 (M+H$^+$).

EXAMPLE 43 trans-4-[4-(2-Phenoxy-ethylamino)-cyclohexyl]-phenol a) Cis-[4-(4-Benzyloxy-phenyl)-cyclohexyl]-(2-phenoxy-ethyl)-amine and Trans-[4-(4-Benzyloxy-phenyl)-cyclohexyl]-(2-phenoxy-ethyl)-amine A mixture of 4-(4-benzyloxy-phenyl)-cyclohexanone (8.2 g, 29 mmol), benzyloxyhydroxylamine hydrochloride (4.7 g, 29 mmol) and ethanol was heated for 2 h. at reflux. The solvent was removed and the residue was crystallized to give white crystals (10.2 g, 90%) of the benzyloxy-oxime of 4-(4-benzyloxy-phenyl)-cyclohexanone. The latter was refluxed for 4 days with LiAlH$_4$ (4 g, 105 mmol) in THF (300 ml). After the addition of $H_2O$ (30 ml), NaOH 15% (30 ml) and $H_2O$ (30 ml), the solids were removed by filtration and the filtrate evaporated. The residue was partioned between $H_2O$ and methylene chloride and the organic layer was dried and evaporated. The residue was purified by chromatography ($SiO_2$, $CH_2Cl_2$—MeOH—aq.NH$_3$ 140:10:1) to give a mixture of cis and trans 4-(4-benzyloxy-phenyl)-cyclohexyl-amine (3.8 g) which was not separated at this stage. A portion of this mixture (1 g, 3.5 mmol) together with 2-phenoxyethyl bromide (0.78 g, 3.55 mmol), $K_2CO_3$ (1 g) and 2-butanone (20 ml) was refluxed for 3 days. The mixture was evaporated and $H_2O$ was added. Extraction with $CH_2Cl_2$ gave after drying and evaporation of the solvent a residue which was purified by chromatography ($SiO_2$, $CH_2Cl_2$—MeOH 98:2) to give cis-[4-(4-benzyloxy-phenyl)-cyclohexyl]-(2-phenoxy-ethyl)-amine (140 mg, colorless oil, MS: m/e=402.5 (M+H$^+$)) and trans-[4-(4-benzyloxy-phenyl)-cyclohexyl]-(2-phenoxy-ethyl)-amine (200 mg, white solid, Mp. 95–98°, MS: m/e=402.5 (M+H$^+$)).

b) trans-4-[4-(2-Phenoxy-ethylamino)-cyclohexyl]-phenol

Following the general method of example 22b, trans-[4-(4-benzyloxy-phenyl)-cyclohexyl]-(2-phenoxy-ethyl)-amine was hydrogenated to give trans-4-[4-(2-phenoxy-ethylamino)-cyclohexyl]-phenol as white crystals. Mp. 160–162°, MS: m/e=312.2 (M+H$^+$).

EXAMPLE 44 trans-4-[4-[Methyl-(2-p-tolyloxy-ethyl)-amino]-cyclohexyl]-phenol a) trans-[4-(4-Benzyloxy-phenyl)-cyclohexyl]-methyl-(2-p-tolyloxy-ethyl)-amine A mixture of trans-2-{[4-(4-benzyloxy-phenyl)-cyclohexyl]-methyl-amino}-ethanol (0.3 g, 0.88 mmol), p-cresol (96 mg, 0.88 mmol), triphenylphosphine (232 mg, 0.88 mmol), diethyl-azodicarboxylate (154 mg, 0.88 mmol) and THF was stirred at rt for 3h. The solvent was evaporated and the rsidue was treated with MeOH/$H_2O$ (3:1, 50 ml) and hexane (50 ml). The aq. layer was extracted with hexane (30 ml). The combined hexane extracts were dried and evaporated. The residue was purified by chromatography ($SiO_2$, $CH_2Cl_2$—MeOH 95:5) to give trans-[4-(4-benzyloxy-phenyl)-cyclohexyl]-methyl-(2-p-tolyloxy-ethyl)-amine (135 mg, 69%, white solid, MS: m/e=430.5 (M+H$^+$)).

b) trans-4-[4-[Methyl-(2-p-tolyloxy-ethyl)-amino]-cyclohexyl]-phenol

Following the general method of example 22b, trans-[4-(4-benzyloxy-phenyl)-cyclohexyl]-methyl-(2-p-tolyloxy-ethyl)-amine (200 mg) was hydrogenated to give trans-4-[4-[methyl-(2-p-tolyloxy-ethyl)-amino]-cyclohexyl]-phenol (110 mg; 70%) as white crystals. MS: m/e=340.3 (M+H$^+$).

EXAMPLE 45 cis-4-[4-[Methyl-(2-p-tolyloxy-ethyl)-amino]-cyclohexyl]-phenol a) cis-[4-(4-Benzyloxy-phenyl)-cyclohexyl]-methyl-(2-p-tolyloxy-ethyl)-amine Following the general procedure of example 44a, cis-2-{[4-(4-benzyloxy-phenyl)-cyclohexyl]-methyl-amino}- ethanol (100 mg)and p-cresol (32 mg) were converted to cis-[4-(4-benzyloxy-phenyl)-cyclohexyl]-methyl-(2-p-tolyloxy-ethyl)-amine (60 mg; 47%) light yellow oil, MS: m/e=430.5 (M+H+)).

b) cis-4-[4-[Methyl-(2-p-tolyloxy-ethyl)-amino]-cyclohexyl]-phenol

Following the general method of example 22b, cis-[4-(4-benzyloxy-phenyl)-cyclohexyl]-methyl-(2-p-tolyloxy-ethyl)-amine (60 mg) was hydrogenated to give cis-4-[4-[methyl-(2-p-tolyloxy-ethyl)-amino]-cyclohexyl]-phenol (33 mg; 70%) as a colorless oil. MS: m/e=340.3 (M+H+).

EXAMPLE 46 trans-4-(4-{[2-(4-Fluoro-phenoxy)-ethyl]-methyl-amino}-cyclohexyl)-phenol a) trans [4-(4-Benzyloxy-phenyl)-cyclohexyl]-[2-(4-fluoro-phenoxy)-ethyl]-methyl-amine Following the general procedure of example 44a trans-2-{[4-(4-benzyloxy-phenyl)-cyclohexyl]-methyl-amino}-ethanol (300 mg) and 4-fluoro-phenol (99 mg) were converted to trans[4-(4-benzyloxy-phenyl)-cyclohexyl]-[2-(4-fluoro-phenoxy)-ethyl]-methyl-amine (208 mg; 54%) light yellow solid, MS: m/e=434.4 (M+H+)).

b) trans-4-(4-{[2-(4-Fluoro-phenoxy)-ethyl]-methyl-amino}-cyclohexyl)-phenol

Following the general method of example 22b, trans-[4-(4-benzyloxy-phenyl)-cyclohexyl]-[2-(4-fluoro-phenoxy)-ethyl]-methyl-amine (200 mg) was hydrogenated to give trans-4-(4-{[2-(4-fluoro-phenoxy)-ethyl]-methyl-amino}-cyclohexyl)-phenol as a light yellow solid (110 mg; 69%. MS: m/e=344.3 (M+H+)).

EXAMPLE 47 trans-4-{4-[Methyl-(2-m-tolyloxy-ethyl)-amino]-cyclohexyl}-phenol a) trans-[4-(4-Benzyloxy-phenyl)-cyclohexyl]-methyl-(2-m-tolyloxy-ethyl)-amine Following the general procedure of example 44a, trans-2-{[4-(4-benzyloxy-phenyl)-cyclohexyl]-methyl-amino}-ethanol (300 mg) and m-cresol (108 mg) were converted to trans-[4-(4-benzyloxy-phenyl)-cyclohexyl]-methyl-(2-m-tolyloxy-ethyl)-amine (148 mg; 39% light yellow solid, MS: m/e=430.5 (M+H+)).

b) trans-4-{4-[Methyl-(2-m-tolyloxy-ethyl)-amino]-cyclohexyl}-phenol

Following the general method of example 22b, trans-[4-(4-benzyloxy-phenyl)-cyclohexyl]-methyl-(2-m-tolyloxy-ethyl)-amine (140 mg) was hydrogenated to give trans-4-{4-[Methyl-(2-m-tolyloxy-ethyl)-amino]-cyclohexyl}-phenol (110 mg; 99%) as a light yellow solid. MS: m/e= 340.3 (M+H+).

EXAMPLE 48 trans-4-{4-[Methyl-(2-o-tolyloxy-ethyl)-amino]-cyclohexyl}-phenol a) cis-2-{[4-(4-Benzyloxy-phenyl)-cyclohexyl]-methyl-amino}-ethanol and trans-2-{[4-(4-Benzyloxy-phenyl)-cyclohexyl]-methyl-amino}-ethanol Following the general method of example 3, cis-2-{[4-(4-benzyloxy-phenyl)-cyclohexyl]-methyl-amino}-ethanol, (193 mg; 7% light yellow solid, MS: m/e=340.3 (M+H+)) trans-2-{[4-(4-benzyloxy-phenyl)-cyclohexyl]-methyl-amino}-ethanol (1.3 g; 45% white crystals, MS: m/e=340.3 (M+H+)) were prepared from 4-(4-benzyloxy-phenyl)-cyclohexanone (2.4 g; 8.6 mmol) and 2-methylamino-ethanol (0.64 g; 8.6 mmol).

b) trans-[4-(4-Benzyloxy-phenyl)-cyclohexyl]-methyl-(2-o-tolyloxy-ethyl)-amine

Following the general procedure of example 44a, trans-2-{[4-(4-benzyloxy-phenyl)-cyclohexyl]-methyl-amino}-ethanol (300 mg) and o-cresol (96 mg) were converted to trans-[4-(4-benzyloxy-phenyl)-cyclohexyl]-methyl-(2-o-tolyloxy-ethyl)-amine (187 mg; 49% light yellow solid, MS: m/e=430.5 (M+H+)).

c) trans-4-{4-[Methyl-(2-o-tolvloxy-ethyl)-amino]-cyclohexyl}-phenol

Following the general method of example 22b, trans-[4-(4-benzyloxy-phenyl)-cyclohexyl]-methyl-(2-o-tolyloxy-ethyl)-amine (170 mg) was hydrogenated to give trans-4-{4-[methyl-(2-o-tolyloxy-ethyl)-amino]-cyclohexyl}-phenol as a white solid.(120 mg; 89%; MS: m/e=340.3 (M+H+)).

EXAMPLE 49

(RS)-1-[cis-4-(4-Benzyloxy-phenyl)-cyclohexylamino]-3-phenyl-propan-2-ol and(RS)-1-[trans-4-(4-Benzyloxy-phenyl)-cyclohexylamino]-3-phenyl-propan-2-ol a) (RS)-1-[cis-4-(4-Benzyloxy-phenyl)-cyclohexylamino]-3-phenyl-propan-2-ol and (RS)-1-[trans-4-(4-Benzyloxy-phenyl)-cyclohexylamino]-3-phenyl-propan-2-ol A mixture of cis and trans 4-(4-benzyloxy-phenyl)-cyclohexyl-amine (preparation see under 43a, 1.0 g, 3.55 mmol), MeOH (100 ml) and 2,3-epoxypropyl-benzene (480 mg, 3.55 mmol) was refluxed for 3 days. Another portion of and 2,3-epoxypropyl-benzene (480 mg, 3.55 mmol) was added and stirring was continued for 2 days. The solvent was evaporated and the residue was purified by chromatography (SiO$_2$, AcOEt-hexane 1:1) to give (RS)-1-[cis-4-(4-benzyloxy-phenyl)-cyclohexylamino]-3-phenyl-propan-2-ol (430 mg, colorless oil, MS: m/e=416.3 (M+H+)) and (RS)-1-[trans-4-(4-benzyloxy-phenyl)-cyclohexylamino]-3-phenyl-propan-2-ol (85 mg, white crystals, Mp. 137.5–138, MS: m/e=416.3 (M+H+)).

b) (RS)-4-[cis-4-(2-Hydroxy-3-phenyl-propylamino)-cyclohexyl]-phenol

Following the general method of example 22b, (RS)-1-[cis-4-(4-benzyloxy-phenyl)-cyclohexylamino]-3-phenyl-propan-2-ol (410 mg; 0.99 mmol) was hydrogenated to give (RS)-4-[cis-4-(2-hydroxy-3-phenyl-propylamino)-cyclohexyl]-phenol (240 mg; 75%) as white crystals. Mp. 52–57°, MS: m/e=326.4 (M+H+).

EXAMPLE 50

(RS)-4-[trans-4-(2-Hydroxy-3-phenyl-propylamino)-cyclohexyl]-phenol

Following the general method of example 22b, (RS)-1-[trans-4-(4-benzyloxy-phenyl)-cyclohexylamino]-3-phenylpropan-2-ol (65 mg; 0.16 mmol) was hydrogenated to give (RS)-4-[trans-4-(2-hydroxy-3-phenyl-propylamino)-cyclohexyl]-phenol (39 mg; 77%) as white crystals. Mp. 56–62°, MS: m/e=326.5 (M+H$^+$).

EXAMPLE 51 cis-(4-Phenyl-cyclohexyl)-(3-phenyl-propyl)-amine and trans-(4-phenyl-cyclohexyl)-(3-phenyl-propyl)-amine Following the general method of example 3, (but using AcOEt-hexane 1:1 for the chromatography), cis-(4-phenyl-cyclohexyl)-(3-phenyl-propyl)-amine, (330 mg; 7%) light yellow oil, MS: m/e=294.4 (M+H$^+$)) and trans-(4-phenyl-cyclohexyl)-(3-phenyl-propyl)-amine (660 mg; 20% white solid, MS: m/e=294.4 (M+H$^+$)) were prepared from 4-phenyl-cyclohexanone (2 g; 11.5 mmol) and 3-phenyl-propylamine (1.55 g; 11.5 mmol).

EXAMPLE 52 cis-[4-(4-Nitro-phenyl)-cyclohexyl]-(3-phenyl-propyl)-amine and trans-[4-(4-Nitro-phenyl)-cyclohexyl]-(3-phenyl-propyl)-amine Following the general method of example 3, cis-[4-(4-nitro-phenyl)-cyclohexyl]-(3-phenyl-propyl)-amine, (orange oil, MS: m/e=294.4 (M+H$^+$)) and trans-[4-(4-nitro-phenyl)-cyclohexyl]-(3-phenyl-propyl)-amine (light pink crystals, MS: m/e=294.4 (M+H$^+$)) were prepared from 4-(4-nitro-phenyl)-cyclohexanone and 3-phenyl-propylamine (6.2 g; 45.6 mmol). The trans isomer (9.3 g; 60%) could be removed from the crude mixture of isomers by crystallization with ether. The mother liquor was then purified by chromatography as described in example 3 to give the pure cis isomer (2.8 g; 18%).

EXAMPLE 53 trans-4-[4-(3-Phenyl-propylamino)-cyclohexyl]-phenylamine

Following the general method of example 22b, trans-[4-(4-nitro-phenyl)-cyclohexyl]-(3-phenyl-propyl)-amine (200 mg; 0.59 mmol) was hydrogenated to give trans-4-[4-(3-phenyl-propylamino)-cyclohexyl]-phenylamine (160 mg; 88%) as light orange crystals. Mp. 60–63°, MS: m/e=309.3 (M+H$^+$).

EXAMPLE 54 trans-Methyl-[4-(4-nitro-phenyl)-cyclohexyl]-(3-phenyl-propyl)-amine

Following the general method of example 39a, trans-[4-(4-nitro-phenyl)-cyclohexyl]-(3-phenyl-propyl)-amine (3.0 g; 8.9 mmol) was N-methylated to give trans-methyl-[4-(4-nitro-phenyl)-cyclohexyl]-(3-phenyl-propyl)-amine (2.2 g; 70%) as light yellow crystals. Mp. 55–56°, MS: m/e=353.3 (M+H$^+$).

EXAMPLE 55 trans-4-{4-[Methyl-(3-phenyl-propyl)-amino]-cyclohexyl}-phenylamine

Following the general method of example 22b, trans-methyl-[4-(4-nitro-phenyl)-cyclohexyl]-(3-phenyl-propyl)-amine (1.6 g; 4.5 mmol) was hydrogenated to give trans-4-{4-[methyl-(3-phenyl-propyl)-amino]-cyclohexyl}-phenylamine (1.35 g; 92%) as an orange oil which solidified on standing. MS: m/e=323.4 (M+H$^+$).

EXAMPLE 56 trans-N-(4-{4-[Methyl-(3-phenyl-propyl)-amino]-cyclohexyl}-phenyl)-methanesulfonamide A mixture of trans-4-{4-[methyl-(3-phenyl-propyl)-amino]-cyclohexyl}-phenylamine (300 mg, 093 mmol), pyridine (10 ml) and methanesulfochloride (118 mg, 1.02 mmol) was stirred at 0°. After 2 h additional methanesulfochloride (118 mg, 1.02 mmol) was added, and stirring was continued for 24 h. The solvent was evaporated and the residue was purified by chromatography (CH$_2$Cl$_2$—MeOH—aq. NH$_3$ 140:10:1) to give trans-N-(4-{4-[methyl-(3-phenyl-propyl)-amino]-cyclohexyl}-phenyl)-methanesulfonamide (306 mg, 82%) as an orange oil which solidified on standing. MS: m/e=401.6 (M+H$^+$).

EXAMPLE 57

(RS)-4-[trans-4-[Methyl-(1-methyl-3-phenyl-propyl)-amino]-cyclohexyl]-phenol a) (RS)-[trans-4-(4-Benzyloxy-phenyl)-cyclohexyl]-methyl-(1-methyl-3-phenyl-propyl)-amine Following the general method of example 39a, (RS)-[trans-4-(4-benzyloxy-phenyl)-cyclohexyl]-(1-methyl-3-phenyl-propyl)-amine (800 mg; 1.9 mmol) was N-methylated to give (RS)-[trans-4-(4-benzyloxy-phenyl)-cyclohexyl]-methyl-(1-methyl-3-phenyl-propyl)-amine (530 mg; 64%) as a colorless oil which solidified on standing. Mp. 54.5–55.5°, MS: m/e=428.5 (M+H$^+$).

b) (RS)-4-[trans-4-[Methyl-(1-methyl-3-phenyl-propyl)-amino]-cyclohexyl]-phenol

Following the general method of example 22b, (RS)-[trans-4-(4-benzyloxy-phenyl)-cyclohexyl]-methyl-(1-methyl-3-phenyl-propyl)-amine (410 mg; 0.96 mmol) was hydrogenated to give (RS)-4-[trans-4-[methyl-(1-methyl-3-phenyl-propyl)-amino]-cyclohexyl]-phenol (165 mg; 51%) as white crystals. MS: m/e=338.3 (M+H$^+$).

EXAMPLE 58

4-[trans-4-[(RS)-1-Methyl-3-phenyl-propylamino)-cyclohexyl]-phenol

Following the general method of example 22b, (RS)-[trans-4-(4-benzyloxy-phenyl)-cyclohexyl]-(1-methyl-3-phenyl-propyl)-amine (300 mg; 0.72 mmol) was hydrogenated to give 4-[trans-4-[(RS)-1-methyl-3-phenyl-propylamino)-cyclohexyl]-phenol (168 mg; 72%) as white crystals. Mp. 155–160°, MS: m/e=324.4 (M+H$^+$).

EXAMPLE 59

4-[cis-4-[(RS)-1-Methyl-3-phenyl-propylamino)-cyclohexyl]-phenol a) (RS)-[cis-4-(4-Benzyloxy-phenyl)-cyclohexyl]-(1-methyl-3-phenyl-propyl)-amine and (RS)-[trans-4-(4-Benzyloxy-phenyl)-cyclohexyl]-(1-methyl-3-phenyl-propyl)-amine Following the general method of example 3, (RS)-[cis-4-(4-benzyloxy-phenyl)-cyclohexyl]-(1-methyl-3-phenylpropyl)-amine (1.90 g; 43% light brown oil, MS: m/e=414.4 (M+H$^+$)) and (RS)-[trans-4-(4-benzyloxy-phenyl)-cyclohexyl]-(1-methyl-3-phenyl-propyl)-amine (1.26 g; 29% light yellow solid, Mp. 70–72°, MS: m/e=414.4 (M+H$^+$)) were prepared from 2-(4-methoxyphenyl)-cyclohexanone (3.0 g; 10.7 mmol) and 3-amino-1-phenylbutane (1.6 g; 10.7 mmol).

b) 4-[cis-4-[(RS)-1-Methyl-3-phenyl-propylamino)-cyclohexyl]-phenol

Following the general method of example 22b, (RS)-[cis-4-(4-benzyloxy-phenyl)-cyclohexyl]-(1-methyl-3-phenyl-propyl)-amine (1.6 g; 3.9 mmol) was hydrogenated to give 4-[cis-4-[(RS)-1-methyl-3-phenyl-propylamino)-cyclohexyl]-phenol (369 mg; 30%) as white crystals. Mp. 44–49°, MS: m/e=324.4 (M+H$^+$).

EXAMPLE 60 trans-4-[4-(3-p-Tolyl-propylamino)-cyclohexyl]-phenol a) cis-[4-(4-Benzyloxy-phenyl)-cyclohexyl]-(3-p-tolyl-propyl)-amine and trans-[4-(4-Benzyloxy-phenyl)-cyclohexyl]-(3-p-tolyl-propyl)-amine A mixture of cis and trans 4-(4-benzyloxy-phenyl)-cyclohexyl-amine (preparation see under example 43a, 1.25 g, 4.44 mmol), K$_2$CO$_3$ (1.23 g, 8.88 mmol), 1-(3-Bromo-propyl)-4-methyl-benzene (1.18 g, 4.44 mmol) and 2-butanone was stirred at 80° for 48 h. Water was then added and the products were extracted with EtOAc. The organic layer was dried (Na2SO$_4$), evaporated and the residue was purified by chromatography (SiO$_2$, CH$_2$Cl$_2$—MeOH—aq. NH$_3$ 140:10:1) to give cis-[4-(4-benzyloxy-phenyl)-cyclohexyl]-(3-p-tolyl-propyl)-amine (180 mg; 10 %) as a light yellow solid (MS: m/e=414.4 (M+H$^+$))and trans-[4-(4-benzyloxy-phenyl)-cyclohexyl]-(3-p-tolyl-propyl)-amine (38 mg; 2%) as a light yellow solid (MS: m/e=414.4 (M+H$^+$)).

b) trans-4-[4-(3-p-Tolyl-propylamino)-cyclohexyl]-phenol

Following the general method of example 22b, trans-[4-(4-benzyloxy-phenyl)-cyclohexyl]-(3-p-tolyl-propyl)-amine (35 mg) was hydrogenated to give trans-4-[4-(3-p-Tolyl-propylamino)-cyclohexyl]-phenol (20 mg; 73%) as a white solid. MS: m/e=324.4 (M+H$^+$).

EXAMPLE 61 trans-4-(4-{[3-(4-Fluoro-phenyl)-propyl]-methyl-aminol-cyclohexyl)-phenol a) trans-[4-(4-Benzyloxy-phenyl)-cyclohexyl]-[3-(4-fluoro-phenyl)-propyl]-methyl-amine Following the general method of example 39a, trans-[4-(4-benzyloxy-phenyl)-cyclohexyl]-[3-(4-fluoro-phenyl)-propyl]-amine (700 mg) was N-methylated to give trans-[4-(4-benzyloxy-phenyl )-cyclohexyl]-[3-(4-fluoiro-phenyl )-propyl]-methyl-amine as a light yellow solid (650 mg; 90%), MS: m/e=432.4 (M+H$^+$)).

b) trans-4-(4-{[3-(4-Fluoro-phenyl)-propyl]-methyl-amino}-cyclohexyl)-phenol

Following the general method of example 22b, trans-[4-(4-benzyloxy-phenyl)-cyclohexyl]-[3-(4-fluoro-phenyl)-propyl]-methyl-amine(600 mg) was hydrogenated to give trans-4-(4-{[3-(4-fluoro-phenyl)-propyl]-methyl-amino}-cyclohexyl)-phenol (200 mg; 42%) as a white solid. MS: m/e=342.3 (M+H$^+$).

EXAMPLE 62 trans-4-[4-[3-(4-Fluoro-phenyl)-propylamino]-cyclohexyl}-phenol a) trans-[4-(4-Benzyloxy-phenyl )-cyclohexyl]-[3-(4-fluoro-phenyl)-propyl]-amine Following the general method of example 3 trans-[4-(4-benzyloxy-phenyl)-cyclohexyl]-[3-(4-fluoro-phenyl)-propyl]-amine (135 mg; 13% white solid, MS: m/e=418.4 (M+H$^+$)) was prepared from 2-(4-methoxyphenyl)-cyclohexanone (0.7 g) and 3-(4-fluorophenyl)propylamine (0.4 g). In this case the cis isomer was not isolated.

b) trans-4-[4-[3-(4-Fluoro-phenyl )-propylamino]-cyclohexyl]-phenol

Following the general method of example 22b, trans-[4-(4-benzyloxy-phenyl)-cyclohexyl]-[3-(4-fluoro-phenyl)-propyl]-amine (130 mg) was hydrogenated to give trans-4-[4-[3-(4-fluoro-phenyl)-propylamino]-cyclohexyl]-phenol (100 mg; 98%) as a white solid. MS: m/e=328.3 (M+H$^+$).

EXAMPLE 63

(RS)-4-[trans-4-[(3-Hydroxy-3-phenyl-propyl)-methyl-amino]-cyclohexyl]-phenol a) (RS)-3-[[trans-4-(4-Benzyloxy-phenyl)-cyclohexyl]-methyl-amino]-1-phenyl-propan-1-ol Following the general method of example 39a, (RS)-3-[trans-4-(4-benzyloxy-phenyl)-cyclohexylamino]-1-phenyl-propan-1-ol (300 mg) was N-methylated to give (RS)-3-[[trans-4-(4-benzyloxy-phenyl)-cyclohexyl]-methyl-amino]- 1-phenyl-propan-1-ol (270 mg; 87%) as a white solid. MS: m/e=430.5 (M+H$^+$).

b) (RS)-4-[trans-4-[(3-Hydroxy-3-phenyl-propyl)-methyl-amino]-cyclohexyl]-phenol Following the general method of example 22b, (RS)-3-[[trans-4-(4-benzyloxy-phenyl)-cyclohexyl]-methyl-amino]-1-phenyl-propan-1-ol (200 mg) was hydrogenated to give (RS)-4-[trans-4-[(3-hydroxy-3-phenyl-propyl)-methyl-amino]-cyclohexyl]-phenol as a white solid (150 mg; 95%). MS: m/e=340.3 (M+H$^+$).

EXAMPLE 64

(RS)-4-[trans-4-(3-Hydroxy-3-phenyl-propylamino)-cyclohexyl]-phenol a) (RS)-3-[trans-4-(4-Benzyloxy-phenyl)-cyclohexylamino]-1-phenyl-propan- 1-ol Following the general method of example 3 (RS)-3-[trans-4-(4-benzyloxy-phenyl)-cyclohexylamino]-1-phenyl-propan-1-ol (840 mg; 10%) white crystals, MS: m/e=416.3 (M+H$^+$)) was prepared from 2-(4-methoxyphenyl)-cyclohexanone (5.56 g) and 3-hydroxy-3-phenyl-propylamine (3.0 g) (for the preparation of this amine: see T. M. Koenig, D. Mitchell, Tetrahedron Letters, 1994, 1339–1342). In this case, the cis isomer was not isolated.

b) (RS)-4-[trans-4-(3-Hydroxy-3-phenyl-propylamino)-cyclohexyl]-phenol

Following the general method of example 22b, (RS)-3-[trans-4-(4-benzyloxy-phenyl)-cyclohexylamino]-1-phenylpropan-1-ol (200 g) was hydrogenated to give (RS)-4-[trans-4-(3-hydroxy-3-phenyl-propylamino)-cyclohexyl]-phenol (120 mg; 77%) as a white solid. MS: m/e=326.3 (M+H$^+$).

EXAMPLE 65

(RS)-4-[trans-4-[(1-Hydroxymethyl-3-phenyl-propyl)-methyl-amino]-cyclohexyl]-phenol a) (RS)-2-[trans-4-(4-Benzyloxy-phenyl)-cyclohexyl]-methyl-amino]-4-phenyl-butan-1-ol Following the general method of example 39a, (RS)-2-ltrans-4-(4-benzyloxy-phenyl)-cyclohexylamino]-4-phenyl-butan-1-ol (500 mg, 1.116 mmol) was N-methylated to give (RS)-2-[[trans-4-(4-benzyloxy-phenyl)-cyclohexyl]-methyl-amino]-4-phenyl-butan-1-ol as a colorless oil (357 mg, 69%, MS: m/e=444.4 (M+H$^+$)).

b) (RS)-4-[trans-4-[(1-Hydroxymethyl-3-phenyl-propyl)-methyl-amino]-cyclohexyl]-phenol Following the general method of example 22b, (RS)-2-[[trans-4-(4-benzyloxy-phenyl)-cyclohexyl]-methyl-amino]-4-phenyl-butan-1-ol (250 mg, 0.56 mmol) was hydrogenated to give (RS)-4-[trans-4-[(1-hydroxymethyl-3-phenyl-propyl)-methyl-amino]-cyclohexyl]-phenol as a white solid (190 mg, 95%, MS: m/e=354.4 (M+H$^+$).

EXAMPLE 66

(RS)-4-[trans-4-(1-Hydroxymethyl-3-phenyl-propylamino)-cyclohexyl]-phenol a) (RS)-2-Amino-4-phenyl-butan-1-ol Following the general procedure of example 40b, DL-homophenylalanine (5.0 g, 27.9 mmol) was reduced with LiAlH$_4$ to give (RS)-2-amino-4-phenyl-butan-1-ol (3.6 g, 78%, MS: m/e=166 (M+H$^+$)) as a light yellow solid.

b) (RS)-2-[cis-4-(4-Benzyloxy-phenyl)-cyclohexylamino]-4-phenyl-butan-1-ol and (RS)-2-[trans-4-(4-Benzyloxy-phenyl)-cyclohexylamino]-4-phenyl-butan-1-ol Following the general method of example 3 (RS)-2-[cis-4-(4-benzyloxy-phenyl)-cyclohexylamino]-4-phenyl-butan-1-ol (white crystals, 600 mg, 6.6%, MS: m/e=430.5 (M+H$^+$)) and (RS)-2-[trans-4-(4-benzyloxy-phenyl)-cyclohexylamino]-4-phenyl-butan-1-ol (4.5 g, 50%, white crystals, MS: m/e=430.5 (M+H$^+$)) were prepared from 2-(4-methoxyphenyl)-cyclohexanone (5.9 g, 21 mmol) and (RS)-2-amino-4-phenyl-butan-1-ol (3.48 g, 21 mmol).

c) (RS)-4-[trans-4-(1-Hydroxymethyl-3-phenyl-propylamino)-cyclohexyl]-phenol

Following the general method of example 22b, (RS)-2-[trans-4-(4-benzyloxy-phenyl)-cyclohexylamino]-4-phenyl-butan-1-ol (250 mg, 0.58 mmol) was hydrogenated to give (RS)-4-[trans-4-(1-hydroxymethyl-3-phenyl-propylamino)-cyclohexyl]-phenol as a white solid (160 mg, 81%, MS: m/e=340.3 (M+H$^+$)).

EXAMPLE 67

(RS)-4-[trans-4-[(4-Hydroxy-3-phenyl-butyl)-methyl-amino]-cyclohexyl]-phenol a) (RS)-4-[[trans-4-(4-Benzyloxy-phenyl)-cyclohexyl]-methyl-amino]-2-phenyl-butan-1-ol Following the general method of example 39a, (RS)-4-[trans-4-(4-benzyloxy-phenyl)-cyclohexylamino]-2-phenyl-butan-1-ol (500 mg, 1.16 mmol) was N-methylated to give (RS)-4-[[trans-4-(4-benzyloxy-phenyl)-cyclohexyl]-methyl-amino]-2-phenyl-butan-1-ol as a colorless oil (285 mg, 55%, MS: m/e=444.4 (M+H$^+$)).

b) (RS)-4-[trans-4-[(4-Hydroxy-3-phenyl-butyl)-methyl-amino]-cyclohexyl]-phenol

Following the general method of example 22b, (RS)-4-[[trans-4-(4-benzyloxy-phenyl)-cyclohexyl]-methyl-amino]-2-phenyl-butan-1-ol (240 mg, 0.54 mmol) was hydrogenated to give (RS)-4-[trans-4-[(4-hydroxy-3-phenyl-butyl)-methyl-amino]-cyclohexyl]-phenol as white crystals (79 mg, 41%, MS: m/e=354.4 (M+H$^+$)).

EXAMPLE 68

(RS)-4-[trans-4-(4-Hydroxy-3-phenyl-butylamino)-cyclohexyl]-phenol a) (RS)-4-[cis-4-(4-Benzyloxy-phenyl)-cyclohexylamino]-2-phenyl-butan-1-ol and (RS)-4-[trans-4-(4-Benzyloxy-phenyl)-cyclohexylamino]-2-phenyl-butan-1-ol Following the general method of example 3 (RS)-4-[cis-4-(4-benzyloxy-phenyl)-cyclohexylamino]-2-phenyl-butan-1-ol (white solid, 910 mg, 12%, MS: m/e=430.5 (M+H$^+$)) and (RS)-4-[trans-4-(4-benzyloxy-phenyl)-cyclohexylamino]-2-phenyl-butan-1-ol (940 mg, 13%, white crystals, Mp. 140–142°, MS: m/e=430.5 (M+H$^+$)) were prepared from 2-(4-methoxyphenyl)-cyclohexanone (4.9 g, 17.55 mmol) and (RS)-4-Amino-2-phenyl-butan-1-ol (2.9 g, 17.55 mmol).

b) (RS)-4-[trans-4-(4-Hydroxy-3-phenyl-butylamino)-cyclohexyl]-phenol

Following the general method of example 22b, (RS)-4-[trans-4-(4-benzyloxy-phenyl)-cyclohexylamino]-2-phenyl-butan-1-ol (300 mg, 0.67 mmol) was hydrogenated to give (RS)-4-[trans-4-(4-hydroxy-3-phenyl-butylamino)-cyclohexyl]-phenol as a white crystals (210 mg, 89%, MS: m/e=340.3 (M+H$^+$)).

EXAMPLE 69

(RS)-4-[trans-4-[(2-Hydroxymethyl-3-phenyl-propyl)-methyl-amino]-cyclohexyl]-phenol a) (RS)-2-Benzyl-3-[[trans-4-(4-benzyloxy-phenyl)-cyclohexyl]-methyl-amino]-propan-1-ol Following the general method of example 39a, (RS)-2-benzyl-3-[trans-4-(4-benzyloxy-phenyl)-cyclohexylamino]-propan-1-ol (300 mg, 0.7 mmol) was N-methylated to give (RS)-2-benzyl-3-[[trans-4-(4-benzyloxy-phenyl)-cyclohexyl]-methyl-amino]-propan-1-ol as a colorless oil (300 mg, 97%, MS: m/e=444.4 (M+H$^+$)).

b) (RS)-4-[trans-4-[(2-Hydroxymethyl-3-phenyl-propyl)-methyl-amino]-cyclohexyl]-phenol Following the general method of example 22b, (RS)-2-benzyl-3-[[trans-4-(4-benzyloxy-phenyl)-cyclohexyl]-methyl-amino]-propan-1-ol (250 mg, 0.56 mmol) was hydrogenated to give (RS)-4-[trans-4-[(2-hydroxymethyl-3-phenyl-propyl)-methyl-amino]-cyclohexyl]-phenol as white crystals (190 mg, 95%, MS: m/e=354.3 (M+H$^+$)).

EXAMPLE 70

(RS)-4-[trans-4-(2-Hydroxymethyl-3-phenyl-propylamino)-cyclohexyl]-phenol a) (RS)-2-Benzyl-3-[cis-4-(4-benzyloxy-phenyl)-cyclohexylamino]-propan-1-ol and (RS)-2-Benzyl-3-[trans-4-(4-benzyloxy-phenyl)-cyclohexylamino]-propan- 1-ol Following the general method of example 3 (RS)-2-benzyl-3-[cis-4-(4-benzyloxy-phenyl)-cyclohexylamino]-propan-1-ol (white solid, 870 mg, 12%, MS: m/e=430.5 (M+H$^+$)) and (RS)-2-benzyl-3-[trans-4-(4-benzyloxy-phenyl)-cyclohexylamino]-propan-1-ol (2.83 g, 38%, white crystals, MS: m/e=430.5 (M+H$^+$)) were prepared from 2-(4-methoxyphenyl)-cyclohexanone (4.9 g, 17.5 mmol) and (RS)-3-amino-2-benzyl-propan-1-ol (2.9 g, 17.5 mmol).

b) (RS)-4-Itrans-4-(2-Hydroxymethyl-3-phenyl-propylamino)-cyclohexyl]-phenol Following the general method of example 22b, (RS)-2-benzyl-3-[trans-4-(4-benzyloxy-phenyl)-cyclohexylamino]-propan-1-ol (250 mg, 0.58 mmol) was hydrogenated to give (RS)-4-[trans-4-(2-hydroxymethyl-3-phenyl-propylamino)-cyclohexyl]-phenol as a white solid (184 mg, 93%, MS: m/e=340.3 (M+H$^+$)).

EXAMPLE 71 cis-4-[1-Hydroxy-4-(3-phenyl-propylamino)-cyclohexyl]-phenol a) 4-(4-Benzyloxy-phenyl)-4-hydroxy-cyclohexanone

To a solution of the Grignard reagent prepared from Magnesium turnings (2.33 g, 96 mmol) and 4-benzyloxybromobenzene (25 g, 95 mmol) in THF (150 ml), 1,4-Cyclohexanedione monoethylene ketal (10 g, 64 mmol) in THF (150 ml) was added. After completeion of the reaction, the solution was added to 200 ml of aq. NH$_4$Cl and extracted with CH$_2$Cl$_2$. Drying and evaporation of the organic layer gave a residue which was crystallised from AcOEt-hexane to give 8-(4-benzyloxy-phenyl)-1,4-dioxa-spiro[4.5]decan-8-ol (17.5 g, 54%, MS: m/e=340 (M$^+$)).

Hydrolysis (72 h at r.t.) of this intermadiate (9 g, 26.4 mmol) with H$_2$O (80 ml) and trifluoroacetic acid (18.2 ml) gave after extraction with CH$_2$Cl$_2$ 4-(4-benzyloxy-phenyl)-4-hydroxy-cyclohexanone (6.39 g, 81.5%, MS: m/e=296 (M$^+$)).

b) cis-1-(4-Benzyloxy-phenyl)-4-(3-phenyl-propylamino)-cyclohexanol

Following the general method of example 3 cis-1-(4-benzyloxy-phenyl)-4-(3-phenyl-propylamino)-cyclohexanol (light yellow solid, 250 mg, 18%, MS: m/e=416.3 (M+H$^+$)) was prepared from 4-(4-benzyloxy-phenyl)-4-hydroxy-cyclohexanone (1 g, 3.37 mmol) and 3-phenylpropylamine (0.456 g, 3.37 mmol).

c) cis-4-[1-Hydroxy-4-(3-phenyl-propylamino)-cyclohexyl]-phenol

Following the general method of example 22b, cis-1-(4-benzyloxy-phenyl)-4-(3-phenyl-propylamino)-cyclohexanol (200 mg, 0.48 mmol) was hydrogenated to cis-4-[1-hydroxy-4-(3-phenyl-propylamino)-cyclohexyl]-phenol as white crystals (from acetonitrile, 85 mg, 55%, MS: m/e=326.4 (M+H$^+$)).

EXAMPLE 72 trans-4-[1-Hydroxy-4-(3-phenyl-propylamino)-cyclohexyl]-phenol a) (1,4-Dioxa-spiro[4.5]dec-8-yl)-(3-phenyl-propyl)-amine hydrochloride (1:1)

A mixture of cyclohexanedione monoethylene ketal (4 g, 25.6 mmol), 3-phenylpropylamin (3.46 g, 25.6 mmol), pTosOH (catalytic amount) and toluene (100 ml) was refluxed overnight in a Dean-Stark apparatus. The solvent was then evaporated and THF (100 ml), MeOH (10 ml) and NaBH$_3$CN (1.89 g) were added. The pH was adjusted to 3–4 by HCl/MeOH addition. After stirring for 4 h, the mixture was treated with sat. NaHCO$_3$ solution (150 ml) and extracted with CH$_2$Cl$_2$. The organic layer was evaporated and the residue was purified by chromatography (SiO$_2$, CH$_2$Cl$_2$—MeOH—aq. NH$_3$ 140:10:1) to give a yellow oil (4.01 g). This was dissolved in MeOH (10 ml) and HCl/MeOH was added dropwise. Ether was added (100 ml) and the white precipitate was collected to afford (1,4-Dioxa-spiro[4.5]dec-8-yl)-(3-phenyl-propyl)-amine hydrochloride (1:1) (3.8 g, 48%, MS: m/e=276.3 (M+H$^+$)).

b) 4-(3-Phenyl-propylamino)-cyclohexanone

A mixture of (1,4-dioxa-spiro[4.5]dec-8-yl)-(3-phenyl-propyl)-amine hydrochloride (1:1) (3.35 g, 10.7 mmol), H$_2$O (25 ml) and trifluoroacetic acid (2.47 ml, 32.2 mmol) was left at r.t for 48 h. NaHCO$_3$ (10%, 100 ml) was added and the solution was extracted with CH$_2$Cl$_2$. Drying of the organic layer (Na$_2$SO$_4$) and evaporation left 4-(3-phenyl-propylamino)-cyclohexanone as a slightly coloured oil (2.4 g, 97%, MS: m/e=232.2 (M+H$^+$)).

c) (4-Oxo-cyclohexyl)-(3-phenyl-propyl)-carbamic acid benzyl ester

A mixture of 4-(3-phenyl-propylamino)-cyclohexanone (1.9 g, 8.21 mmol), K$_2$CO$_3$ (1.15 g, 8.3 mmol), benzyl chloroformate (1.42 g, 8.3 mmol) and CH$_2$Cl$_2$ (20 ml) was stirred at r.t for 1.5 h. H$_2$O (50 ml) was added, and the mixture was extracted with CH$_2$Cl$_2$. The organic layer was dried (Na$_2$SO$_4$), evaporated and the residue was purified by chromatography (SiO$_2$, CH$_2$Cl$_2$—MeOH 95:5) to give (4-Oxo-cyclohexyl)-(3-phenyl-propyl)-carbamic acid benzyl ester as a yellow oil (2.7 g, 90%, MS: m/e=365(M$^+$)).

d) trans-4-[1-Hydroxy-4-(3-phenyl-propylamino)-cyclohexyl]-phenol

To the Grignard reagent prepared from Magnesium turnings (0.3 g, 12.3 mmol) and 4-benzyloxybromobenzene (2.7 g, 10.26 mmol) in THF (l00ml) was added (4-Oxo-cyclohexyl)-(3-phenyl-propyl)-carbamic acid benzyl ester (2.5 g, 6.84 mmol) in THF (50 ml). After refluxing for 2 h, cooling to 0°, addition of aq. NH$_4$Cl (100 ml), extraction with CH$_2$Cl$_2$, drying (Na$_2$SO$_4$) and evaporation of the organic layer, and purification of the residue by chromatography (SiO$_2$, CH$_2$Cl$_2$—MeOH 98:2) gave the benzylated intermediate (565 mg, 15%). Following the general method of example 22b this intermediate (200 mg, 0.364 mmol) was hydrogenated to give trans-4-[1-hydroxy-4-(3-phenyl-propylamino)-cyclohexyl]-phenol as light yellow crystals (53 mg, 45%, MS: m/e=326.4 (M+H$^+$)).

EXAMPLE 73

(1RS,3RS,4RS)-4-[3-Methyl-4-[methyl-(3-phenyl-propyl)-amino]-cyclohexyl]-phenol a) (1RS,2RS,4RS)-[4-(4-Benzyloxy-phenyl)-2-methyl-cyclohexyl]-methyl-(3-phenyl-propyl)-amine Following the general method of example 39a, (1RS,2RS,4RS)-[4-(4-benzyloxy-phenyl)-2-methyl-cyclohexyl]-(3- phenyl-propyl)-amine (160 mg, 0.39 mmol) was N-methylated to give (1RS,2RS,4RS)-[4-(4-benzyloxy-phenyl)-2-methyl-cyclohexyl]-methyl-(3-phenyl-propyl)-amine as a colorless oil (116 mg, 70%, MS: m/e=428.6 (M+H$^+$)).

b) (1RS,3RS,4RS)-4-[3-Methyl-4-[methyl-(3-phenyl-propyl)-amino]-cyclohexyl]-phenol Following the general method of example 22b, (1RS,2RS,4RS)-[4-(4-benzyloxy-phenyl)-2-methyl-cyclohexyl]-methyl-(3-phenyl-propyl)-amine (100 mg, 0.23 mmol) was hydrogenated to give (1RS,3RS,4RS)-4-[3-methyl-4-[methyl-(3-phenyl-propyl)-amino]-cyclohexyl]-phenol as a light-yellow oil (42 mg, 53%, MS: m/e=338.3 (M+H$^+$)).

EXAMPLE 74

(1RS,3RS,4RS)-4-[3-Methyl-4-(3-phenyl-propylamino)-cyclohexyl]-phenol a) (2RS,4RS)-4-(4-Benzyloxy-phenyl)-2-methyl-cyclohexanone To a solution of LDA (23.6 mmol) in THF (80 ml) at −75°, a solution of 4-(4-benzyloxy-phenyl)-cyclohexanone (6 g, 21.4 mmol) in THF (50 ml) was added over 20 min. After 1 h at −75°, iodomethane (3.2 g, 22.5 mmol) was added and stirring was continued at RT overnight. The solution was then acidified and partitioned between H$_2$O and AcOEt. Extraction with AcOEt, drying of the organic layers, evaporation and purification of the residue by chromatography (SiO$_2$, AcOEt-hexane 1:6) gave a first fraction (3.15 g) of monomethyl derivatives and a second fraction (1.02 g) of dimethyl derivatives. From the the first fraction the title compound (2RS,4RS)-4-(4-benzyloxy-phenyl)-2-methyl-cyclohexanone (1.941 g, white crystals, 28%, MS: m/e=294 (M$^+$)) was separated by crystallisation from ether.

b) (1RS,2RS,4RS)-[4-(4-Benzyloxy-phenyl)-2-methyl-cyclohexyl]-(3-phenyl-propyl)-amine Following the general method of example 3 (1RS,2RS,4RS)-[4-(4-benzyloxy-phenyl)-2-methyl-cyclohexyl]-(3-phenyl-propyl)-amine (white solid, 301 mg, 21.4%, MS: m/e=414.4 (M+H$^+$)) was prepared from (2RS,4RS)-4-(4-benzyloxy-phenyl)-2-methyl-cyclohexanone (1.0 g, 3.4 mmol) and 3-phenylpropylamine (0.46 g, 3.4 mmol).

c) (1RS,3RS,4RS)-4-[3-Methyl-4-(3-phenyl-propylamino)-cyclohexyl]-phenol

Following the general method of example 22b, (1RS,2RS,4RS)-[4-(4-benzyloxy-phenyl)-2-methyl-cyclohexyl]-(3-phenyl-propyl)-amine (110 mg, 0.27 mmol) was hydrogenated to give (1RS,3RS,4RS)-4-[3-methyl-4-(3-phenyl-propylamino)-cyclohexyl]-phenol as light-yellow crystals (76 mg, 88%, MS: m/e=324.4 (M+H$^+$)).

EXAMPLE 75

4-{4-[Methyl-(3-phenyl-propyl)-amino]-piperidin-1-yl}-phenol

Following the general method of example 1, [1-(4-methoxy-phenyl)-piperidin-4-yl]-methyl-(3-phenyl-propyl)-amine (0.5 g, 1.5 mmol) was converted to 4-{4-[methyl-(3-phenyl-propyl)-amino]-piperidin-1-yl}-phenol, giving 0.22 g (46%) of a white solid. MS: m/e=325.4 (M+H$^+$).

EXAMPLE 76

[1-(4-Methoxy-phenyl)-piperidin-4-yl]-methyl-(3-phenyl-propyl)-amine

Following the general method of example 39a, [1-(4-methoxy-phenyl)-piperidin-4-yl]-(3-phenyl-propyl)-amine (750 mg) was N-methylated to give [1-(4-methoxy-phenyl)-piperidin-4-yl]-methyl-(3-phenyl-propyl)-amine (540 mg; 69%) as a colorless oil. MS: m/e=339.3 (M+H$^+$).

EXAMPLE 77

4-[4-(3-Phenyl-propylamino)-piperidin-1-yl]-phenol

Following the general method of example 1, [1-(4-methoxy-phenyl)-piperidin-4-yl]-(3-phenyl-propyl)-amine (0.5 g, 1.5 mmol) was converted to 4-[4-(3-phenyl-propylamino)-piperidin-1-yl]-phenol, giving 0.2 g (44%) of a white solid. MS: m/e=311.2 (M+H$^+$).

EXAMPLE 78

[1-(4-Methoxy-phenyl)-piperidin-4-yl]-(3-phenyl-propyl)-amine

Following the general procedure of example 40b, N-[1-(4-methoxy-phenyl)-piperidin-4-yl]-3-phenyl-propionamide (1.87 g, 5.53 mmol) was reduced with LiAlH4 to give [1-(4-methoxy-phenyl)-piperidin-4-yl]-(3-phenyl-propyl)-amine (1.64 g, 91%, MS: m/e=325.4 (M+H$^+$)) as a white solid.

EXAMPLE 79

N-[1-(4-Methoxy-phenyl)-piperidin-4-yl]-3-phenyl-propionamide a) 1-(4-Methoxy-phenyl)-piperidin-4-one oxime A mixture of 1-(p-methoxyphenyl)-4-piperidinone (prepared following the procedure reported in: Scherer, T. et al., Recl. Trav. Chim. Pays-Bas (1993), 112(10), 535–48.) (5.13 g, 25 mmol), K$_2$CO$_3$ (6.22 g, 45 mmol), hydroxylamine hydrochloride (2.606 g, 37.5 mmol) and ethanol was refluxed for 20 min. After cooling H$_2$O (50 ml) was added and white crystals of 1-(4-methoxy-phenyl)-piperidin-4-one oxime (4.56 g, 83%, Mp. 116–119°, MS: m/e=220 (M$^+$)) was collected.

b) 1-(4-Methoxy-phenyl)-piperidin-4-yl-amine

A mixture of 1-(4-methoxy-phenyl)-piperidin-4-one oxime (4.55 g, 20.6 mmol), "Red-Al®" (70% in toluene, 23.4 ml) and toluene (10 ml) was heated at 140° for 2 h. After cooling, the reaction mixture was poured on H$_2$O (100 ml). Extraction of the solution with CH$_2$Cl$_2$, drying of the organic layer, evaporation of the solvent and purification of the residue by chromatography (SiO$_2$, CH$_2$Cl$_2$—MeOH—aq. NH$_3$ 140:10:1) gave 1-(4-methoxy-phenyl)-piperidin-4-yl-amine (3.5 g, 89%, white crystals, MS: m/e=207.2 (M+H$^+$)).

c) N-[1-(4-Methoxy-phenyl)-piperidin-4-yl]-3-phenyl-propionamide

A mixture of 3-phenyl propionic acid (360 mg, 2.4 mmol), CDI (410 mg, 2.5 mmol) and DMF (20 ml) was stirred at 50° for 1 h. After cooling to 0°, 1-(4-methoxy-phenyl)-piperidin-4-ylamine (500 mg, 2.4 mmol) was added and stirring continued for 1 h. After the addition of H$_2$O (60 ml) the white precipitate was collected to give N-[1-(4-methoxy-phenyl)-piperidin-4-yl]-3-phenyl-propionamide (618 mg, 76%, MS: m/e=339.3 (M+H$^+$)).

EXAMPLE 80

(3RS,4RS)-4-[3-Methyl-4-(3-phenyl-propylamino)-piperidin-1-yl]-phenol

Following the procedure of example 22b, (3RS,4RS)-[1-(4-benzyloxy-phenyl)-3-methyl-piperidin-4-yl]-(3-phenyl-propyl)-amine (90 mg) was hydrogenated to give (3RS,4RS)-4-[3-methyl-4-(3-phenyl-propylamino)-piperidin-1-yl]-phenol (70 mg; 99% light yellow oil, m/e=325.4 (M+H$^+$)).

EXAMPLE 81

(3RS,4SR)-4-[3-Methyl-4-(3-phenyl-propylamino)-piperidin-1-yl]-phenol a) (RS)-1-(4-Benzyloxy-phenyl)-3-methyl-piperidin-4-one and 1-(4-Benzyloxy-phenyl)-3,3-dimethyl-piperidin-4-one Following the procedure of example 74a, 1-(p-benzyloxyphenyl)-4-piperidinone (4.7 g; 16.7 mmol) (prepared following the procedure reported in: Scherer, T. et al., Recl. Trav. Chim. Pays-Bas (1993), 112(10), 535-48.) was converted to (RS)-1-(4-benzyloxy-phenyl)-3-methyl-piperidin-4-one (710 mg; 14% white solid MS: m/e=296.3 (M+H$^+$)) and 1-(4-benzyloxy-phenyl)-3,3-dimethyl-piperidin-4-one (498 mg; 10% white solid MS: m/e=309 (M$^+$)).

b) (E)- and/or (Z)-1-(4-Benzyloxy-phenyl)-3-methyl-piperidin-4-one oxime

Follwing the procedure of example 79a, (RS)-1-(4-benzyloxy-phenyl)-3-methyl-piperidin-4-one (730 mg) was converted to (E)- and/or (Z)-1-(4-benzyloxy-phenyl)-3-methyl-piperidin-4-one oxime (560 mg; 73% light yellow solid, MS: m/e=311.2 (M+H$^+$)).

c) Mixture of (3RS,4RS)- and (3RS,4SR)-1-(4-benzyloxy-phenyl)-3-methyl-piperidin-4-yl-amine Following the procedure of example 79b (500 mg), (E)- and/or (Z)-1-(4-benzyloxy-phenyl)-3-methyl-piperidin-4-one oxime was converted to a mixture of (3RS,4RS)- and (3RS,4SR)-1-(4-benzyloxy-phenyl)-3-methyl-piperidin-4-yl-amine (410 mg; 86% light yellow solid, MS: m/e=297.3 (M+H$^+$)).

d) (3RS,4RS)-N-[1-(4-Benzyloxy-phenyl)-3-methyl-piperidin-4-yl]-3-phenyl-propionamide and (3RS,4SR)-N-[1-(4-Benzyloxy-phenyl)-3-methyl-piperidin-4-yl]-3-phenyl-propionamide Following the procedure of example 79c, a mixture of (3RS,4RS)- and (3RS,4SR)-1-(4-benzyloxy-phenyl)-3-methyl-piperidin-4-ylamine (395 mg) was conyerted to (3RS,4RS)-N-[1-(4-benzyloxy-phenyl)-3-methyl-piperidin-4-yl]-3-phenyl-propionamide (170 mg; 30%) white solid, m/e=429.5 (M+H$^+$)) and (3RS,4SR)-N-[1-(4-benzyloxy-phenyl)-3-methyl-piperidin-4-yl]-3-phenyl-propionamide (216 mg; 38% white solid, m/e=429.5 (M+H$^+$)) which were separated by chromatography.

e) (3RS,4SR)-[1-(4-Benzyloxy-phenyl)-3-methyl-piperidin-4-yl]-(3-phenyl-propyl)-amine Following the procedure of example 40b, (3RS,4SR)-N-[1-(4-benzyloxy-phenyl)-3-methyl-piperidin-4-yl]-3-phenyl-propionamide (220 mg) was converted to (3RS,4SR)-[1-(4-benzyloxy-phenyl)-3-methyl-piperidin-4-yl]-(3-phenyl-propyl)-amine (200 mg; 94% light yellow solid, m/e=415.4 (M+H$^+$)).

f) (3RS,4RS)-[1-(4-Benzyloxy-phenyl)-3-methyl-piperidin-4-yl]-(3-phenyl-propyl)-amine Following the procedure of example 40b, (3RS,4RS)-N-[1-(4-benzyloxy-phenyl)-3-methyl-piperidin-4-yl]-3-phenyl-propionamide (160 mg) was converted to (3RS,4RS)-[1-(4-benzyloxy-phenyl)-3-methyl-piperidin-4-yl]-(3-phenyl-propyl)-amine (100 mg; 65% light yellow solid, m/e=415.4 (M+H$^+$)).

g) (3RS,4SR)-4-[3-Methyl-4-(3-phenyl-propylamino)-piperidin-1-yl]-phenol

Following the procedure of example 22b, (3RS,4SR)-[1-(4-Benzyloxy-phenyl)-3-methyl-piperidin-4-yl]-(3-phenyl-propyl)-amine (190 mg) was hydrogenated to give (3RS,4SR)-4-[3-Methyl-4-(3-phenyl-propylamino)-piperidin-1-yl] -phenol (134 mg; 90% light yellow oil, m/e=325.4 (M+H$^+$)).

EXAMPLE 82

(RS)-4-[3,3-Dimethyl-4-(3-phenyl-propylamino)-piperidin- 1-yl]-phenol a) (E)- and/or (Z)-1-(4-Benzyloxy-phenyl)-3,3-dimethyl-piperidin-4-one oxime Following the procedure of example 79a, 1-(4-benzyloxy-phenyl)-3,3-dimethyl-piperidin-4-one (450 mg) was converted to (E)- and/or (Z)-1-(4-benzyloxy-phenyl)-3,3-dimethyl-piperidin-4-one oxime which was obtained as a white solid (460 mg; MS: m/e=325.3 (M+H$^+$)).

b) (RS)-1-(4-Benzyloxy-phenyl)-3,3-dimethyl-piperidin-4-yl-amine

Following the procedure of example 79b, (E)- and/or (Z)-1-(4-benzyloxy-phenyl)-3,3-dimethyl-piperidin-4-one oxime (420 mg) was reduced to give (RS)-1-(4-benzyloxy-phenyl)-3,3-dimethyl-piperidin-4-yl-amine (237 mg; 59%) which was obtained as a light yellow solid (MS: m/e=311.2 (M+H$^+$)).

c) (RS)-N-[1-(4-Benzyloxy-phenyl)-3,3-dimethyl-piperidin-4-yl]-3-phenyl-propionamide Following the procedure of example 79c, (RS)-1-(4-benzyloxy-phenyl)-3,3-dimethyl-piperidin-4-ylamine (230 mg) was converted to (RS)-N-[1-(4-benzyloxy-phenyl)-3,3-dimethyl-piperidin-4-yl]-3-phenyl-propionamide (243 mg; 74%) which was obtained as a light brown solid (MS: m/e=443.4 (M+H$^+$)).

d) (RS)-[1-(4-Benzyloxy-phenyl)-3,3-dimethyl-piperidin-4-yl]-(3-phenyl-propyl)-amine Following the procedure of example 40b, (RS)-N-[1-(4-benzyloxy-phenyl)-3,3-dimethyl-piperidin-4-yl]-3-phenyl-propionamide (450 mg) was reduced with LiAlH$_4$ to give (RS)-[1-(4-benzyloxy-phenyl)-3,3-dimethyl-piperidin-4-yl]-(3-phenyl-propyl)-amine as a white solid (260 mg; 60%, MS: m/e=429.4 (M+H$^+$)).

e) (RS)-4-[3,3-Dimethyl-4-(3-phenyl-propylamino)-piperidin-1-yl]-phenol

Following the procedure of example 22b, (RS)-[1-(4-benzyloxy-phenyl)-3,3-dimethyl-piperidin-4-yl]-(3-phenylpropyl)-amine (200 mg) was hydrogenated to give (RS)-4-[3,3-dimethyl-4-(3-phenyl-propylamino)-piperidin-1-yl]-phenol (125 mg; 79%) as a white solid (MS: m/e=339.4 (M+H$^+$)).

EXAMPLE 83

4-[4-(4-Phenyl-butylamino)-piperidin-1-yl]-phenol a) N-[1-(4-Benzyloxy-phenyl)-piperidin-4-yl]-4-phenyl-butyramide Following the procedure of example 79c, 4-phenylbutyric acid (261 mg) and 1-(4-benzyloxy-phenyl)-piperidin-4-yl-amine (450 mg) were converted to N-[1-(4-benzyloxy-phenyl)-piperidin-4-yl]-4-phenyl-butyramide (520 mg; 76%) which was obtained as white crystals (MS: m/e=429.5 (M+H$^+$)).

b) [1-(4-Benzyloxy-phenyl)-piperidin-4-yl]-(4-phenyl-butyl)-amine

Following the procedure of example 40b, N-[1-(4-benzyloxy-phenyl)-piperidin-4-yl]-4-phenyl-butyramide (450 mg) was reduced with LiAlH$_4$ to give [1-(4-benzyloxy-phenyl)-piperidin-4-yl]-(4-phenyl-butyl)-amine (75 mg; 17%) as a light yellow solid (MS: m/e=415.4 (M+H$^+$)).

c) 4-[4-(4-Phenyl-butylamino)-piperidin-1-yl]-phenol

Following the procedure of example 22b, [1-(4-benzyloxy-phenyl)-piperidin-4-yl]-(4-phenyl-butyl)-amine (60 mg) was hydrogenated to give 4-[4-(4-phenyl-butylamino)-piperidin-1-yl]-phenol (34 mg; 72%) as a colorless oil which solidified on standing (MS: m/e=325.4 (M+H$^+$)).

EXAMPLE 84

4-(4-Phenethylamino-piperidin-1-yl)-phenol a) 1-(4-Benzyloxy-phenyl)-piperidin-4-one oxime Following the procedure of example 79a, 1-(4-benzyloxy-phenyl)-piperidin-4-one oxime was prepared from 1-(p-benzyloxyphenyl)-4-piperidinone (9.1 g) (prepared following the procedure reported in: Scherer, T. et al., Recl. Trav. Chim. Pays-Bas (1993), 112(10), 535–48.). It was obtained as a white solid (9.16 g; 96%) MS: m/e=296 (M$^+$)).

b) 1-(4-Benzyloxy-phenyl)-piperidin-4-yl-amine

Following the procedure of example 79b, 1-(4-benzyloxy-phenyl)-piperidin-4-one oxime (8.16 g) was reduced to 1-(4-benzyloxy-phenyl)-piperidin-4-ylamine which was obtained as a light brown solid (4.31 g, MS: m/e=283.1 (M+H$^+$)).

c) N-[1-(4-Benzyloxy-phenyl)-piperidin-4-yl]-2-phenyl-acetamide

Following the procedure of example 79c, 4-phenylacetic acid (338 mg) and 1-(4-benzyloxy-phenyl)-piperidin-4-yl-amine (700 mg) were converted to N-[1-(4-benzyloxy-phenyl)-piperidin-4-yl]-4-phenyl-acetamide (487 mg; 49%) which was obtained as white crystals (MS: m/e=401.4 (M+H$^+$)).

d) [1-(4-Benzyloxy-phenyl)-piperidin-4-yl]-phenethyl-amine

Following the procedure of example 40b, N-[1-(4-benzyloxy-phenyl)-piperidin-4-yl]-2-phenyl-acetamide (200 mg) was reduced with LiAlH$_4$ to give [1-(4-benzyloxy-phenyl)-piperidin-4-yl]-phenethyl-amine (65 mg; 34%) as a white solid (MS: m/e=387.3 (M+H$^+$)).

e) 4-(4-Phenethylamino-piperidin-1-yl)-phenol

Following the procedure of example 22b, [1-(4-benzyloxy-phenyl)-piperidin-4-yl]-phenethyl-amine (50 mg) was hydrogenated to give 4-(4-phenethylamino-piperidin-1-yl)-phenol (22 mg; 57%) as light yellow oil (MS: m/e=297.3 (M+H$^+$)).

EXAMPLE 85 trans-4-[5-(3-Phenyl-propylamino)-[1,3]dioxan-2-yl] l-phenol 1:1 but-2-enedioic acid Following the general procedure of example 40b, trans-N-[2-(4-hydroxy-phenyl)-[1,3]dioxan-5-yl]-3-phenyl-propionamide (2.5 g; 7.6 mmol) was reduced to trans-4-[5-(3-phenyl-propylamino)-[1,3]dioxan-2-yl]-phenol (470 mg; 20%). Treatment with fumaric acid (150 mg) in ether gave the title compound (160 mg; 78%, MS: m/e=314.3 (M+H$^+$)).

EXAMPLE 86 trans-N-[2-(4-Hydroxy-phenyl)-[13]dioxan-5-yl]-3-phenyl-propionamide and cis-N-[2-(4-Hydroxy-phenyl)-[1,3]dioxan-5-yl]-3-phenyl-propionamide a) N-(2-Hydroxy-1-hydroxymethyl-ethyl)-3-phenyl-propionamide The procedure of example 79c was followed, using 3-phenylpropionic acid and serinol. At the end of the reaction, the DMF was evaporated and CH$_2$Cl$_2$ was added to the residue. The white crystalline material was collected and gave pure N-(2-hydroxy-1-hydroxymethyl-ethyl)-3-phenyl-propionamide as a white solid (56%, MS: m/e=224.2 (M+H$^+$)).

b) trans-N-[2-(4-Hydroxy-phenyl)-[1,3]dioxan-5-yl]-3-phenyl-propionamide and cis-N-[2-(4-Hydroxy-phenyl)-[1,3]dioxan-5-yl]-3-phenyl-propionamide A mixture of N-(2-hydroxy-1-hydroxymethyl-ethyl)-3-phenyl-propionamide (1.7 g, 7.6 mmol), toluene (70 ml), 4-hydroxybenzaldehyde (1.856 g, 15.2 mmol) and a catalytic amount of p-toluenesulfonic acid was refluxed for 3 h. The mixture was evaporated and CH$_2$Cl$_2$ was added to the residue. The precipitate was filtered off and recrystallised from hot AcOEt (50 ml). The light brown crystals formed collected yielding trans-N-12-(4-hydroxy-phenyl)-[1,3]dioxan-5-yl]-3-phenyl-propionamide (1.41 g, MS: m/e= 328.2 (M+H$^+$)). The filtrate was concentrated and left at 4° overnight. The newly formed crystals are collected yielding cis-N-[2-(4-hydroxy-phenyl)-[1,3]dioxan-5-yl]-3-phenyl-propionamide (0.401 g, m/e=326.4 (M–H$^+$)).

EXAMPLE A

Tablet Formulation (Wet Granulation)

| Item | Ingredients | 5 mg | 25 mg | 100 mg | 500 mg |
|---|---|---|---|---|---|
| | | mg/tablet | | | |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 835 |

Manufacturing Procedure
1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

Capsule Formulation

| Item | Ingredients | 5 mg | 25 mg | 100 mg | 500 mg |
|---|---|---|---|---|---|
| | | mg/tablet | | | |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:

1. A method of treating a neurodegenerative disease comprising administering to a patient in need of such treatment a therapeutically effective amount of a compound of the general formula

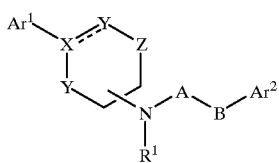

I wherein $Ar^1$ is phenyl, naphthyl or tetrahydronaphthyl, optionally substituted by hydroxy, lower alkoxy, nitro, amino or methanesulfonamide;

$Ar^2$ is phenyl, naphthyl or tetrahydronaphthyl, optionally substituted by lower alkyl or halogen;

X is C, CH, C(OH) or N;

Y is —$CH_2$—, CH or O;

Z —$CH_2$—, —$CH(CH_3)$— or —$C(CH_3)_2$—;

$R^1$ is hydrogen, lower alkyl or acetyl;

A is C=O or —$(CHR^2)_n$—, wherein $R^2$ is hydrogen, lower alkyl or hydroxy-lower alkyl;

B is —$(CH_2)_n$—, O, —$CH(OH)(CH_2)_n$—, —$CH(CH_2OH)(CH_2)_n$—, —$(CH_2)_n$ CH(OH)— or —CH($CH_2OH$)—;

- - - may be a bond; and n is 0–4, or pharmaceutically acceptable acid addition salts thereof.

2. The method in accordance with claim 1, wherein the neurodegenerative disease is selected from the group consisting of stroke, brain trauma, Alzheimer's disease, Parkinson's disease, Huntington's disease, amyotrophic lateral sclerosis, neurodegeneration associated with bacterial sclerosis and neurodegeneration associated with bacterial or viral infection.

3. The method in accordance with claim 1, wherein the compound administered is of the general formula

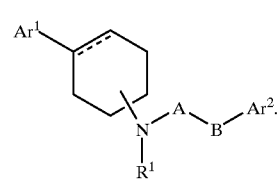

Ia

4. The method in accordance with claim 3, wherein the compound is taken from the group consisting of trans-4-[4-(3-phenyl-propylamino)-cyclohexyl]-phenol, trans-4-[4-[methyl-(3-phenyl-propyl)-amino]-cyclohexyl]-phenol, trans-4-[4-[ethyl-(3-phenyl-propyl)-amino]-cyclohexyl]-phenol, trans-4-[4-(4-phenyl-butylamino)-cyclohexyl]-phenol, trans-4-[4-[3-(4-fluoro-phenyl)-propylamino]-cyclohexyl]phenol, trans-4-(4-[[3-(4-fluoro-phenyl)-propyl]-methyl-amino]-cyclohexyl)-phenol, trans-4-[4-[methyl-(2-p-tolyloxy-ethyl)-amino]-cyclohexyl]-phenol, (RS)-4-[trans-4-(1-hydroxymethyl-3-phenyl-propylamino)-cyclohexyl]-phenol, (RS)-4-[trans-4-(2-hydroxymethyl-3-phenyl-propylamino)-cyclohexyl]-phenol, and trans-N-(4-[4-[methyl-(3-phenyl-propyl)-amino]-cyclohexyl]-phenyl)-methanesulfonamide.

5. The method in accordance with claim 1, wherein the compound administered is of the general formula

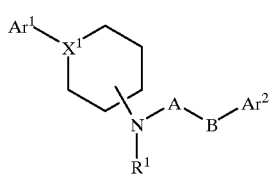

Ib wherein $X^1$ is selected from the group consisting of —C(OH)— and N.

6. The method in accordance with claim 5, wherein the compound is taken from the group consisting of
cis-4-[1-hydroxy-4-(3-phenyl-propylamino)-cyclohexyl]-phenol,
4-[4-[methyl-(3-phenyl-propyl)-amino]-piperidin-1-yl]-phenol and
4-[4-(3-phenyl-propylamino)-piperidin-1-yl]-phenol.

7. The method in accordance with claim 1, wherein the compound administered is of the general formula

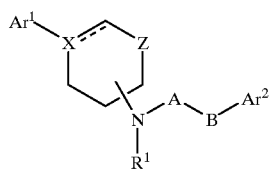

Ic wherein Z is —CH(CH$_3$)— or —C(CH$_3$)$_2$—.

8. The method in accordance with claim 7, wherein the compound is (1RS, 3RS, 4RS)-4-[3-methyl-4-[methyl-(3-phenyl-propyl)-amino]-cyclohexyl]-phenol.

9. The method in accordance with claim 1, wherein the compound administered is of the general formula

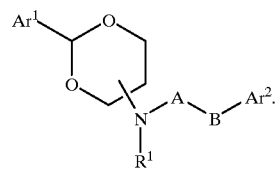

Id

10. The method in accordance with claim 9, wherein the compound is trans-4-[5-(3-phenyl-propylamino)-[1,3]dioxan-2-yl]-phenol.

11. The method in accordance with claim 1, wherein the compound is selected from the group consisting of
trans-4-(4-{[2-(4-fluoro-phenoxy)-ethyl]-methyl-amino}-cyclohexyl)-phenol,
(RS)-4-[trans-4-[methyl-(1-methyl-3-phenyl-propyl)-amino]-cyclohexyl]-phenol,
trans-4-[4-(3-p-tolyl-propylamino)-cyclohexyl]-phenol,
(RS)-4-[trans-4-[(1-hydroxymethyl-3-phenyl-propyl)-methyl-amino]-cyclohexyl]-phenol, and
(1RS,3RS,4RS)-4-[3-methyl-4-(3-phenyl-propylamino)-cyclohexyl]-phenol.

12. The method of treatment according to claim 1, wherein the compound is administered to the patient in an amount from about 0.1 mg to about 1000 mg per day.

13. The method of treatment according to claim 12, wherein the compound is in an amount from about 1 mg to about 500 mg per day.

14. The method of treatment according to claim 13, wherein the compound is in an amount from about 1 mg to about 100 mg per day.

* * * * *